US010520295B2

(12) United States Patent
Cotte et al.

(10) Patent No.: US 10,520,295 B2
(45) Date of Patent: Dec. 31, 2019

(54) DIGITAL HOLOGRAPHIC MICROSCOPE

(71) Applicant: NANOLIVE SA, Ecublens (CH)

(72) Inventors: Yann Cotte, Lausanne (CH);
Pierre-Alain Cotte, Amberg (DE);
Sebastien Equis, Penthalaz (CH);
Andreas Kern, Tübingen (DE)

(73) Assignee: NANOLIVE SA, Ecublens (CH)

( * ) Notice: Subject to any disclaimer, the term of this patent is extended or adjusted under 35 U.S.C. 154(b) by 0 days.

(21) Appl. No.: 15/513,012

(22) PCT Filed: Sep. 18, 2015

(86) PCT No.: PCT/IB2015/057195
§ 371 (c)(1),
(2) Date: Mar. 21, 2017

(87) PCT Pub. No.: WO2016/046714
PCT Pub. Date: Mar. 31, 2016

(65) Prior Publication Data
US 2017/0299371 A1      Oct. 19, 2017

(30) Foreign Application Priority Data

Sep. 22, 2014   (EP) ..................................... 14185718

(51) Int. Cl.
*G01B 9/02* (2006.01)
*G01N 21/45* (2006.01)
(Continued)

(52) U.S. Cl.
CPC ..... *G01B 9/02047* (2013.01); *G01B 9/02068* (2013.01); *G01N 21/453* (2013.01);
(Continued)

(58) Field of Classification Search
CPC ............ G01B 9/02047; G01B 9/02068; G03H 1/268; G03H 1/265; G03H 1/0443;
(Continued)

(56) References Cited

U.S. PATENT DOCUMENTS 8,896,840 B2 * 11/2014 Matsubara ........... G01N 21/453
356/458
2005/0275845 A1   12/2005 Finarov
(Continued)

FOREIGN PATENT DOCUMENTS

EP          2 439 577        4/2012
WO          WO 00/20929      4/2000
(Continued)

OTHER PUBLICATIONS

International Search Report for PCT/IB2015/057195, dated Apr. 11, 2016, 25 pages.
(Continued)

*Primary Examiner* — Hwa Andrew Lee
(74) *Attorney, Agent, or Firm* — Nixon & Vanderhye PC

(57) ABSTRACT

Microscope (2) comprising a coherent light source (4) producing a coherent light beam (7), a light beam guide system (6) comprising a beam splitter (14) configured to split the coherent light beam (7) into a reference beam (7a) and a sample illumination beam (7b), a sample holder (18) configured to hold a sample (1) to be observed, a sample illumination device (28) configured to direct the sample illumination beam (7b) through the sample and into a microscope objective (37), a beam reuniter (16) configured to reunite the reference beam and sample illumination beam after passage of the sample illumination beam through the sample to be observed, and a light sensing system (8) configured to capture at least phase and intensity values of the coherent light beam downstream of the beam reuniter.

18 Claims, 36 Drawing Sheets

(51) Int. Cl.
  *G02B 21/14* (2006.01)
  *G02B 21/36* (2006.01)
  *G02B 26/10* (2006.01)
  *G03H 1/08* (2006.01)
  *G03H 1/26* (2006.01)
  *G03H 1/04* (2006.01)
  *G02B 26/08* (2006.01)
  *G03H 1/00* (2006.01)

(52) U.S. Cl.
  CPC ........... *G02B 21/14* (2013.01); *G02B 21/367* (2013.01); *G02B 26/0816* (2013.01); *G02B 26/108* (2013.01); *G03H 1/0443* (2013.01); *G03H 1/0866* (2013.01); *G03H 1/265* (2013.01); *G03H 1/268* (2013.01); *G03H 2001/005* (2013.01); *G03H 2001/0038* (2013.01); *G03H 2001/0456* (2013.01)

(58) Field of Classification Search
  CPC ......... G03H 1/0866; G03H 2001/0456; G03H 2001/005; G03H 2001/0038; G02B 26/0816; G02B 26/108; G02B 21/14; G02B 21/367; G01N 21/453
  See application file for complete search history.

(56) References Cited

U.S. PATENT DOCUMENTS

2007/0263208 A1* 11/2007 Yelin ............... A61B 5/0066
  356/307
2008/0291518 A1  11/2008 Broome et al.

FOREIGN PATENT DOCUMENTS

WO  WO 2006/104899  10/2006
WO  WO 2011/121523  10/2011
WO  WO 2012/118436  9/2012

OTHER PUBLICATIONS

Sung et al., "Optical diffraction tomography for high resolution live cell imaging", Optics Express, OSA, vol. 17, No. 1, Jan. 5, 2009, pp. 266-277.

Dmitriev et al., "Twin-wave Mach-Zehnder laser interferometer with stabilization of the position of the operating point", Instruments and Experimental Techniques, Consultants Bureau, vol. 19, No. 5/2, Sep. 10, 1976, pp. 1484-1485.

Cotte et al., "Marker-free phase nanoscopy", Nature Photonics, vol. 7, No. 2, Jan. 20, 2013, pp. 113-117.

Tiziani et al., "Optical methods for precision measurements", Optical and Quantum Electronics, vol. 21, No. 4, Jul. 1, 1989, 253-282.

* cited by examiner

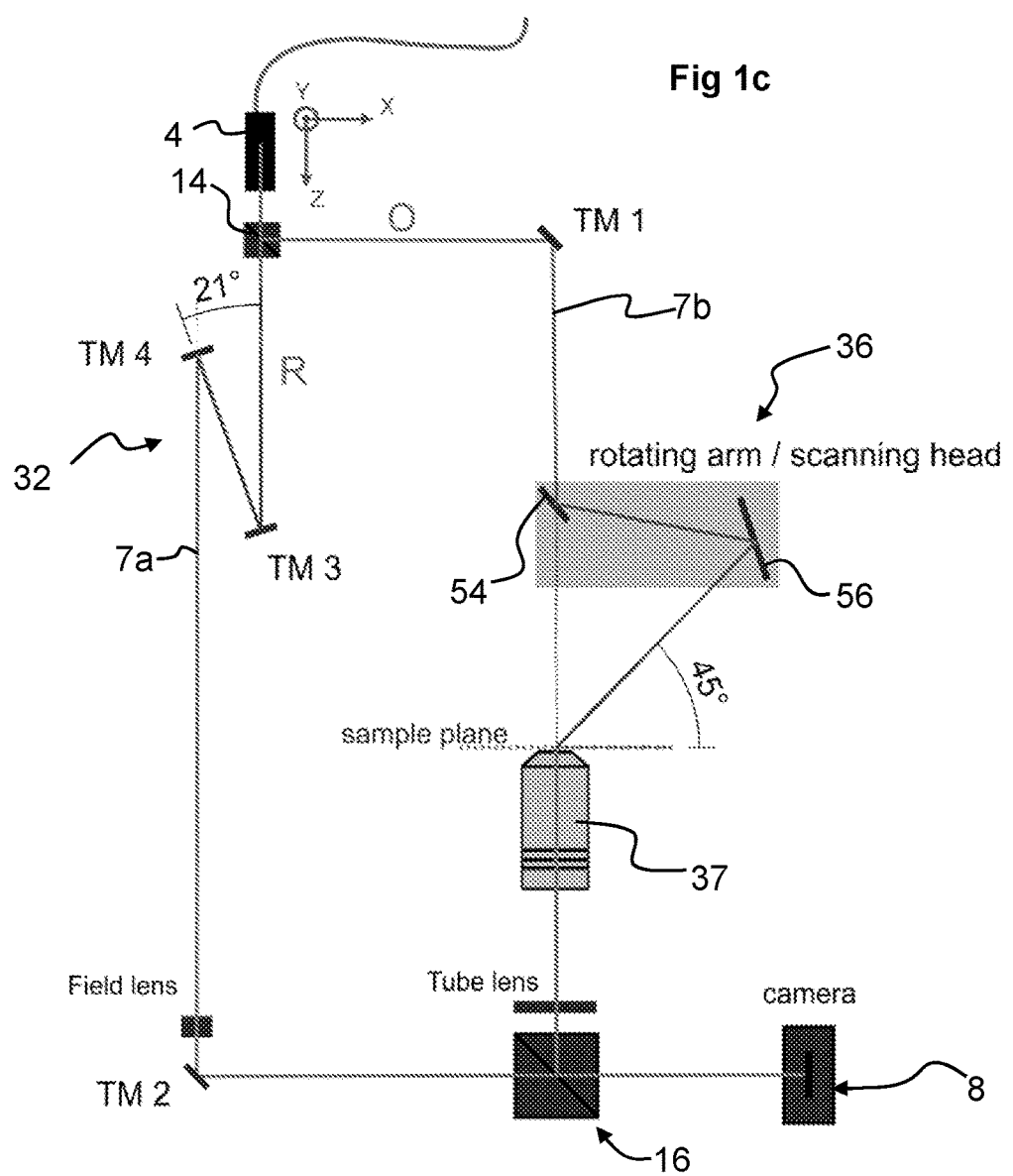

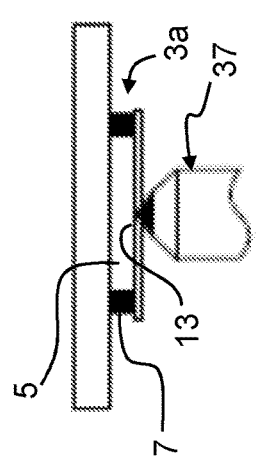
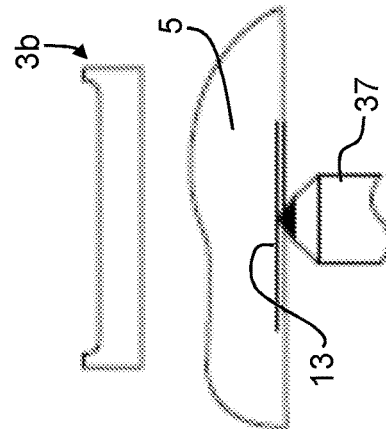
Fig. 3a
Fig. 3b
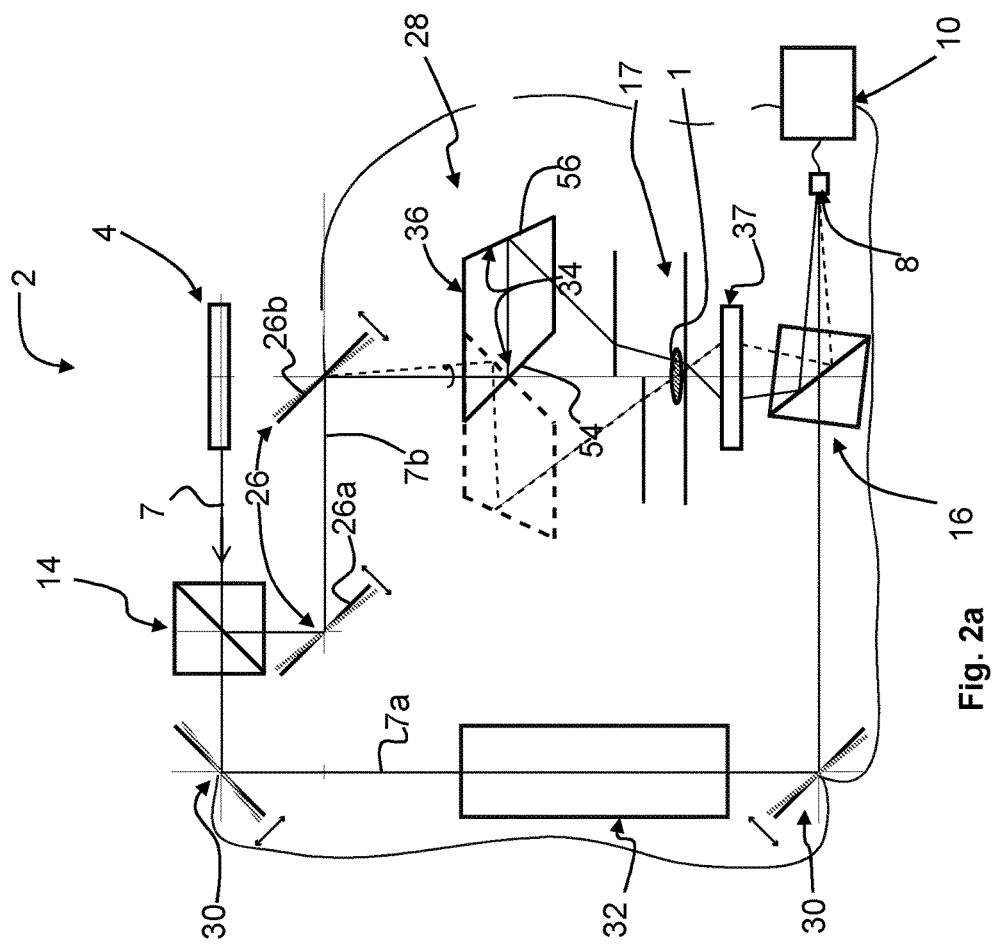
Fig. 2a

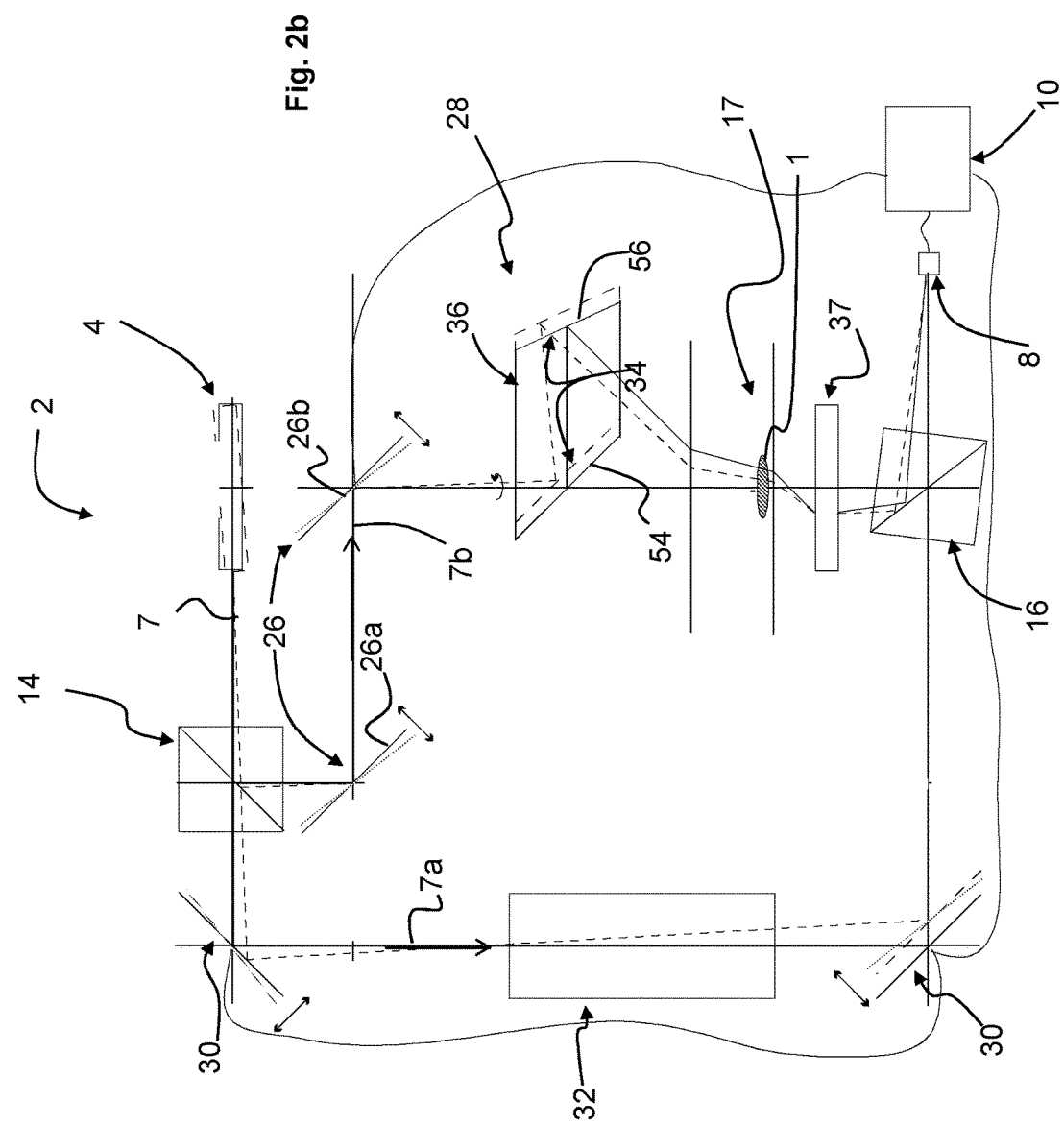

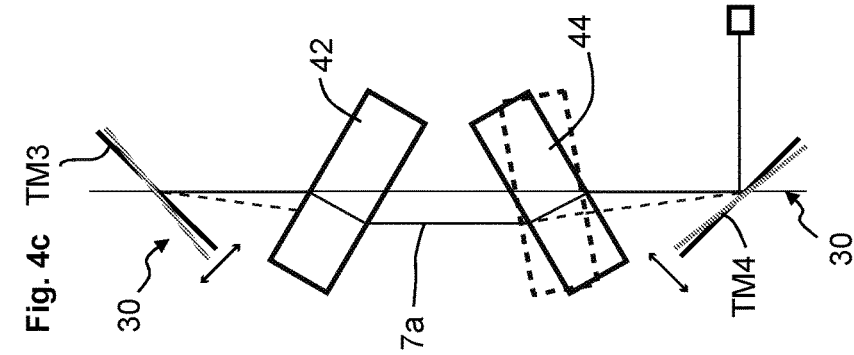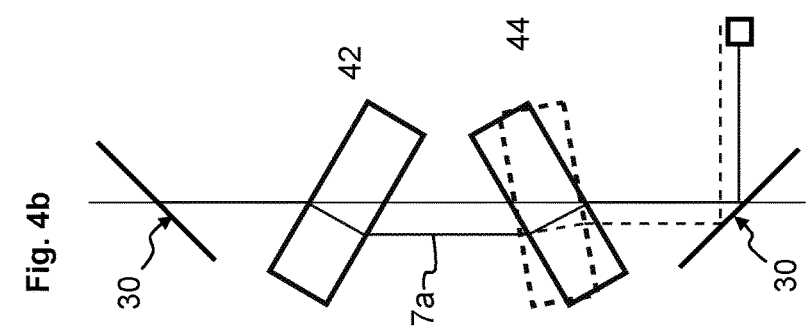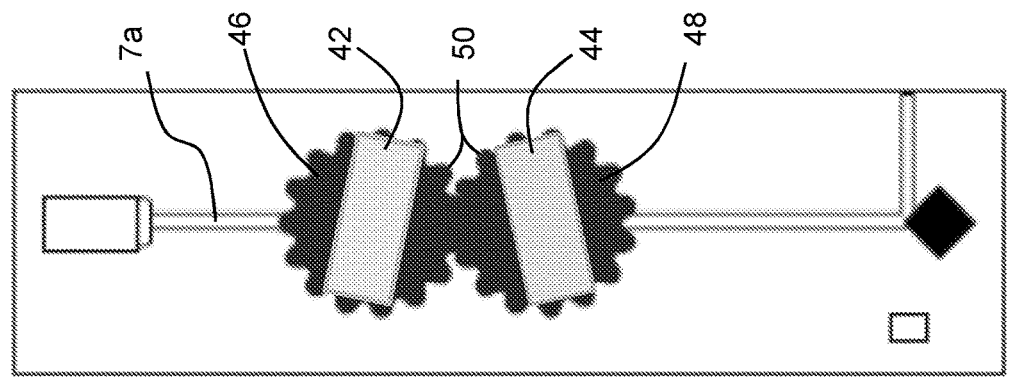

OPD based on tilted mirrors
perfectly synchronized

OPD based on tilted mirrors
unperfectly synchronized

OPD based on tilted mirrors
with 2 tiltable mirrors

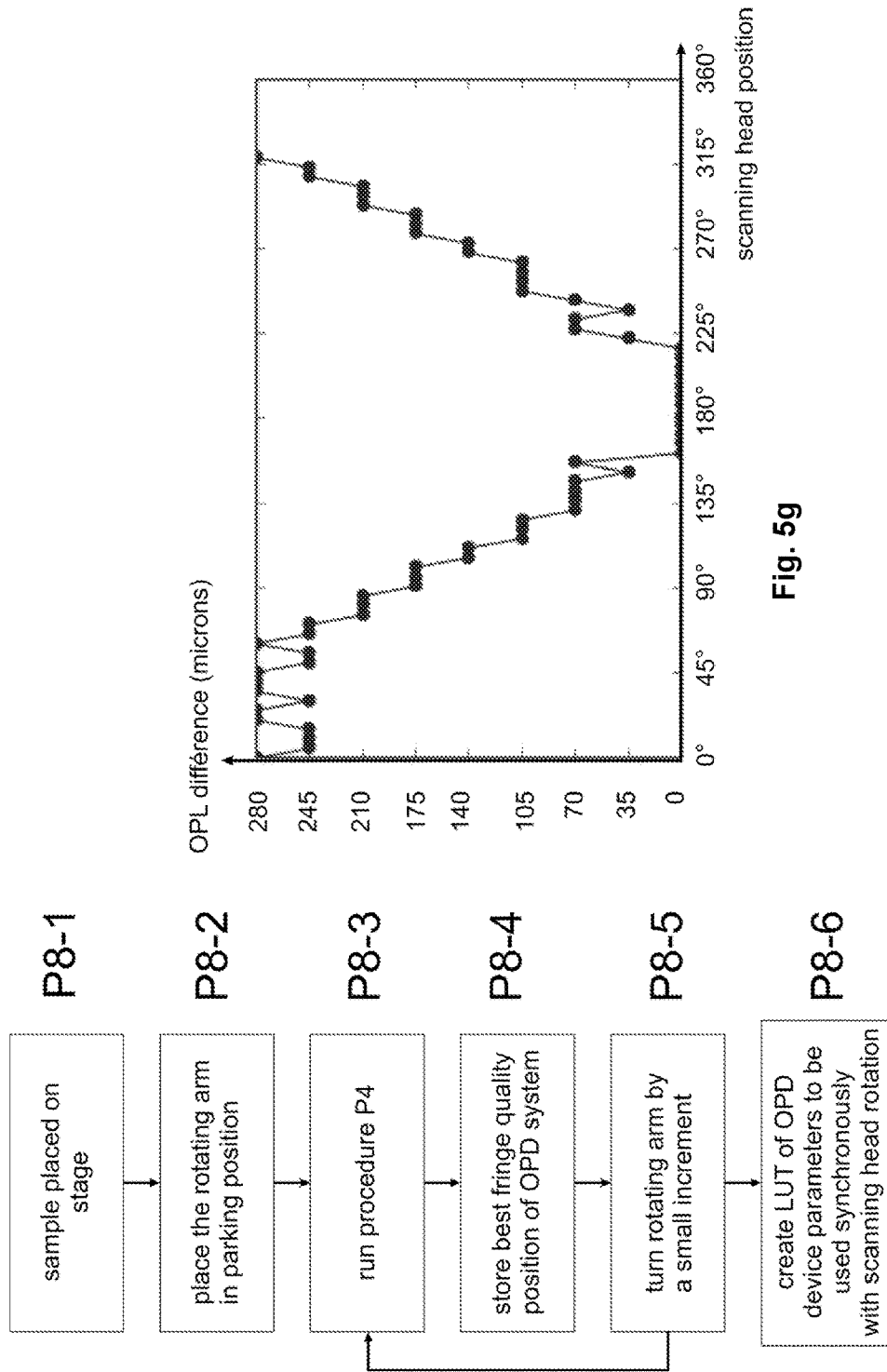

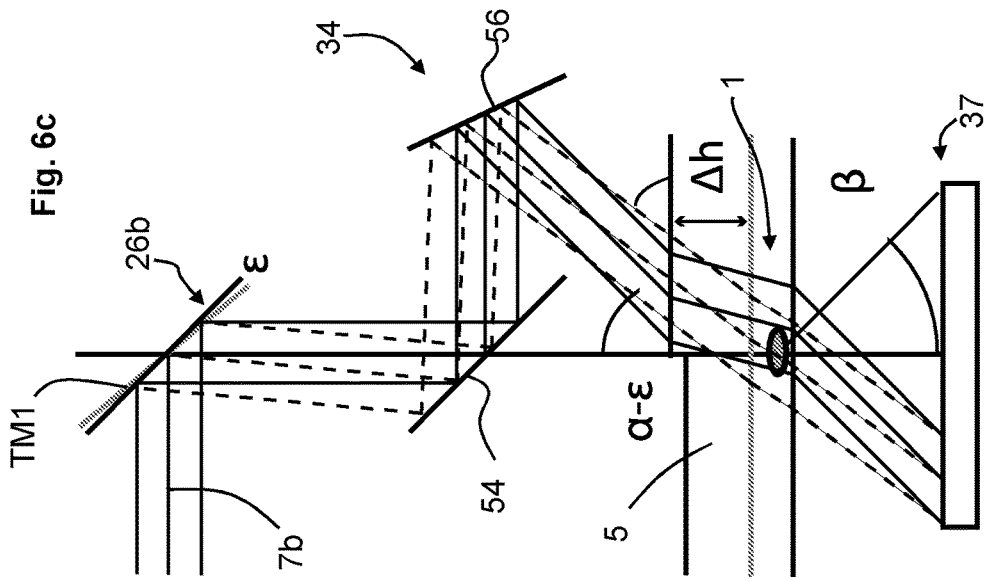
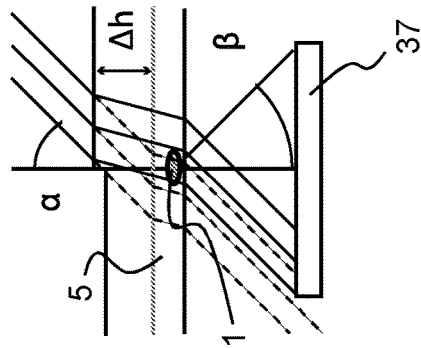
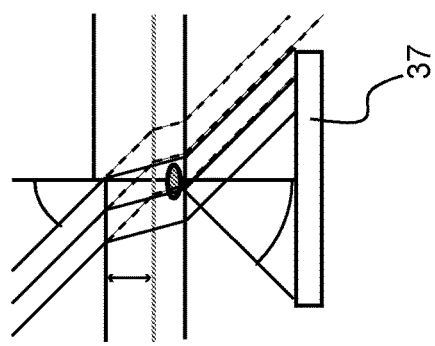

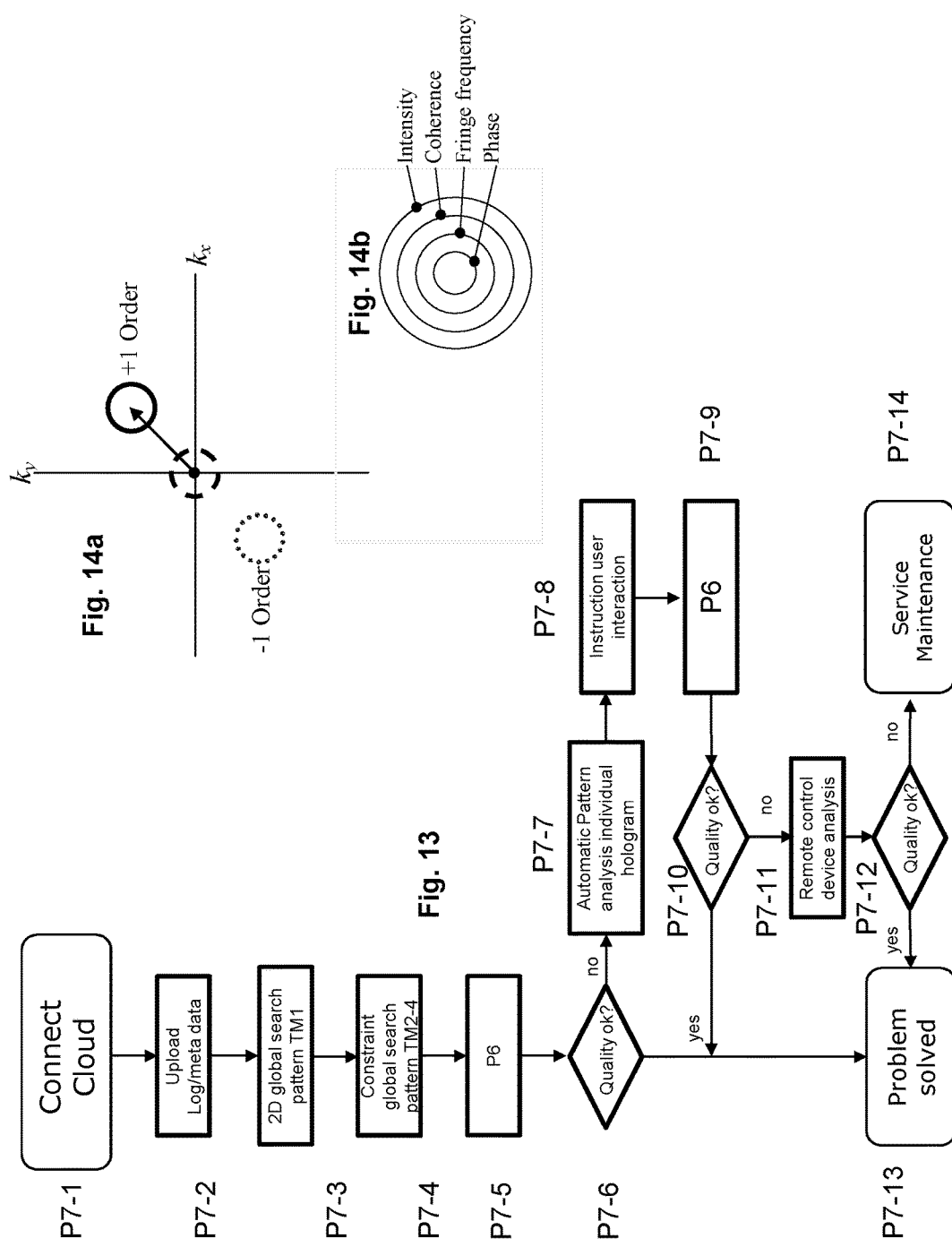

Aberrations – Higher order development
$$Z_n^m(\rho,\varphi) = R_n^m(\rho)\cos(m\varphi)$$
$$Z_n^{-m}(\rho,\varphi) = R_n^m(\rho)\sin(m\varphi),$$

|  | alpha | d | beta | d' | theta | 1" mirror | d" | delta | MEMS | delta |
|---|---|---|---|---|---|---|---|---|---|---|
| default | 45° | 0 | 180° | 65mm | 67.5° | (67.5°) | 0mm | 0mm | 0° | 0mm |
| alpha variable | 45.1 | 0 | 180 | 65 | 67.5 | (57.7°) | 0 | 0.777 | 0.061 | 0.00 |
|  | 45.01 | 0 | 180 | 65 | 67.5 | (67.51°) | 0 | 0.077 | 0.006 | 0.00 |
|  | 45.005 | 0 | 180 | 65 | 67.5 | (67.51°) | 0 | 0.039 | 0.003 | 0.00 |
|  | 45.5 | 0 | 180 | 65 | 67.5 | (67.89°) | 0 | 3.943 | 0.3055 | 0 |
| theta variable | 45 | 0 | 180 | 65 | 67.6 | (67.6°) | 0 | 0.455 | 0.0357 | 0.00 |
|  | 45 | 0 | 180 | 65 | 68 | (68°) | 0 | 2.309 | 0.1788 | 0.00 |
| beta variable | 45 | 0 | 180.5 | 65 | 67.5 | (68°) | 0 | 1.518 | 0.1194 | 0 |
| d' variable | 45 | 0 | 180 | 65.1 | 67.5 | (67.5°) | 0 | 0.1 | 0.00785 | 0 |
|  | 45 | 0 | 180 | 65.5 | 67.5 | (67.5°) | 0 | 0.5 | 0.03928 | 0 |
| d variable | 45 | 0.1 | 180 | 65 | 67.5 | (67.5°) | 0 | 0.2 | 0.0157 | 0.00 |
|  | 45 | 0.5 | 180 | 65 | 67.5 | (67.5°) | 0 | 1 | 0.079 | 0.00 |
| d" variable | 45 | 0.35 | 180 | 65.5 | 67.5 | (67.5°) | 0.5 | 0.2 | 0.0157 | 0.00 |
| alpha & theta variable | 45.5 | 0 | 180 | 65 | 67 | (68°) | 0 | 1.604 | 0.1265 | 0 |
|  | 45.5 | 0 | 180 | 65 | 68 | (69°) | 0 | 6.167 | 0.4843 | 0 |
|  | 45.1 | 0 | 180 | 65 | 67.6 | (67.8°) | 0 | 1.237 | 0.0968 | 0.00 |
| alpha, beta & theta variable | 45.1 | 0 | 180.5 | 65 | 67.6 | (68.3°) | 0 | 2.772 | 0.2165 | 0 |
|  | 45.1 | 0 | 180.1 | 65 | 67.6 | (67.9°) | 0 | 1.543 | 0.1207 | 0.00 |
|  | 45.05 | 0 | 180.05 | 65 | 67.55 | (67.7°) | 0 | 0.769 | 0.0604 | 0 |
|  | 45.025 | 0 | 180.025 | 65 | 67.525 | (67.6°) | 0 | 0.384 | 0.0302 | 0 |
| All parameters variable | 45.025 | 0.1 | 180.025 | 64.9 | 67.525 | (67.6°) | 0.1 | 1.284 | 0.1013 | 0.00 |

|  | alpha | d | beta | d' | theta | d" |
|---|---|---|---|---|---|---|
| diam | 12.7 |  | 25 |  | 25.4 |  |
| angle (°) | 0.025 |  | 0.025 |  | 0.025 |  |
| angle (rad) | 0.000436 |  | 0.000436 |  | 0.000436 |  |
| Wished tolerances | 0.005541 | 0.1 | 0.010908 | 0.1 | 0.011083 | 0.1 |

|  | alpha | d | beta | d' | theta | d" | delta | MEMS | delta |
|---|---|---|---|---|---|---|---|---|---|
| Possible tolerances | 0.01 | 0.1 | 0.01 | 0.1 | 0.01 | 0.1 |  |  |  |
| diam | 12.7 |  | 25 |  | 25.4 |  |  |  |  |
| angle (rad) | 0.000787 |  | 0.0004 |  | 0.000394 |  |  |  |  |
| angle (°) | 0.572958 |  | 0.572958 |  | 0.572958 |  |  |  |  |
| Example | 0.045115 | 0.1 | 0.022918 | 0.1 | 0.022557 | 0.1 | 1.423 | 0.1122 |  |

Fig. 17b

DIGITAL HOLOGRAPHIC MICROSCOPE

This application is the U.S. national phase of International Application No. PCT/M2015/057195 filed 18 Sep. 2015, which designated the U.S. and claims priority to EP Patent Application No. 14185718.5 filed 22 Sep. 2014, the entire contents of each of which are hereby incorporated by reference.

FIELD OF THE INVENTION

The present invention relates to a microscope, in particular a microscope for three dimensional tomographic imaging of biological matter, including cells and microorganisms. The present invention may also be used more generally in the field of three dimensional tomographic imaging of non-biological transparent materials.

BACKGROUND

Microscopes capable of three-dimensional imaging of biological cells and their internal structures are generally based on digital tomographic techniques and are often based on the use of marker dyes to enhance the intensity contrast between components of the cell. Marker dyes however may affect the matter to be observed, particularly in the case of living cells, and also render the procedure more complex. A marker free non-invasive microscopy method based on 3D refractive index computation is described in international patent application PCT/IB2011/051306. The capture of the image data needed to compute a refractive index based image of very small objects with sufficient detail of the internal structure requires however a microscope that is very precise. The precision of conventional microscopes depends on the quality of the lenses and very low manufacturing tolerances in the assembly of the various components of the microscope. This leads to a costly microscope. Moreover, in order to have a high numerical aperture in order to increase the resolution of the captured data, the available working distance and space for the sample to be observed is very limited. This complicates the preparation of the specimen or sample for viewing by the microscope and limits the type of samples that may be observed and the forms in which they may be presented.

SUMMARY OF THE INVENTION

An object of the invention is to provide that a microscope that is easy and economical to implement and to use.

It is advantageous to provide a microscope that is accurate and offers a high resolution, yet that is economical to produce.

It is advantageous to provide a microscope that simplifies the preparation of biological samples to be observed.

It is advantageous to provide a microscope that can be used with various standard or common forms of biological sample containers, including culture dishes for living cells.

It is advantageous to provide a microscope that simplifies the preparation of biological samples to be observed.

It is advantageous to provide a microscope that is reliable.

It is advantageous to provide a microscope that is versatile.

Disclosed herein is a microscope comprising a light source producing a light beam that is at least partially collimated, a light beam guide system comprising a beam splitter configured to split the light beam into a reference beam and a sample illumination beam, a sample observation zone configured to receive a sample to be observed, a beam reuniter configured to reunite the reference beam and sample illumination beam after passage of the sample illumination beam through the sample observation zone, and a light sensing system configured to capture at least phase and intensity values of the light beam downstream of the beam reuniter. In an embodiment the light source may be configured to generate a coherent or partially coherent collimated light beam, in particular a laser beam, for instance a diode laser beam. In a variant the light source may generate incoherent light, for instance white light, that is collimated for instance by means of an optical lens.

According to a first aspect of the invention, the light beam guide system comprises direction change mirrors to direct the reference beam and the sample illumination beam along their respective optical paths, wherein at least one of the direction change mirrors is a pivotally actionable mirror controllable by an electronic control system of the microscope. The control system is configured to generate a mirror angle control signal to automatically control an angle of said at least one pivotally actionable direction change mirror, the mirror angle control signal being based at least partially on a signal of the light beam received, by means of a feedback loop of the control system, by the light sensing system.

In an embodiment, the control signal may be based on both the phase and intensity values of the light beam measured by the light sensing system.

Advantageously, the microscope may be easily calibrated after manufacturing or transport, at regular interval or before each use, by an electronic control of the angle of one or more of the direction change mirrors in the sample illumination and/or in the reference beam path.

According to a second aspect of the invention, the sample illumination device comprises a mirror system configured to direct the sample illumination beam at a non zero illumination angle (non orthoscopic illumination) with respect to an optical axis, and a rotating beam mechanism configured to rotate the angled sample illumination beam at least 360° (2 pi radians) around the optical axis.

The rotating sample illumination beam with a pre-determined illumination angle according to the invention is particularly advantageous over conventional solutions in that it allows to illuminate the microscopic object at a large illumination angle, limited principally by the numerical aperture of the microscope objective, in an arrangement that is low cost compared to lens based solutions. In effect, the rotating beam does not change the beam shape as opposed to lenses or refractive or diffractive elements which thus need to be manufactured with extremely high quality in order to reduce beam shaping, thus increasing production costs as opposed to the solution provided by the present invention. Moreover the rotating beam allows a large working space for the sample thus providing versatility in the size of the samples that may be positioned on the sample holder and viewed by the microscope while significantly reducing the manufacturing costs of the microscope and sensitivity to the quality of the optical elements along the optical path.

According to a third aspect of the invention, the microscope further comprises an optical path difference (OPD) adjustment device configured to adjust the optical path length of the reference beam relative to the sample illumination beam, the OPD adjustment device comprising a first light deviating element and a second light deviating element, each mounted on pivot supports configured to vary the angle of the first light deviating element relative to the second light deviating element, whereby the angles of inclination of the light deviating elements influences at least the optical path difference.

A continuous and accurate adjustment of the optical path difference may thus be achieved. Moreover, if needed, a dynamic adjustment is possible.

In an embodiment, the mirror system of the sample illumination device is mounted in a rotating support and the rotating beam mechanism is formed by the rotating support and a motor drive to rotate the support.

In an embodiment, the rotating beam mechanism comprises rotating tilt actionable mirrors to direct the sample illumination beam on the mirror system of the sample illumination device and wherein the mirror system is mounted on a fixed support.

In an advantageous embodiment, the pivotally actionable mirror is a Microelectromechanical (MEMS) type component.

In an advantageous embodiment, the pivotally actionable mirror is positioned essentially above the sample in line with the optical axis of the microscope objective.

In an advantageous embodiment, the direction change mirrors comprise at least first and second direction change mirrors arranged in the optical path of the sample illumination beam downstream of the beam splitter, both mirrors being pivotally actionable to correct for optical path errors or to change the sample illumination angle.

In an advantageous embodiment, the microscope further comprises a data processing system configured to receive a plurality of image frames data from the light sensing system, said plurality of image frames being generated for at least a 360° rotation of the sample illumination beam around the microscope objective optical axis.

In an advantageous embodiment, the number of frames per 360° captured by the light sensing system and data processing system is greater than 10, preferably greater than 20, more preferably greater than 30.

In an advantageous embodiment, the image frames data are reconstituted by the data processing system, or supplied by the data processing system to an external computing system, for processing into a three dimensional image of the microscopic object.

In an advantageous embodiment, the microscope is configured to generate a three-dimensional image of the microscopic object based on the refractive index distribution of the microscopic object by determining the phase shift of the sample illumination beam after passing through the microscopic object.

Also disclosed herein is a method of controlling a microscope comprising a light source producing a light beam, a light beam guide system comprising a beam splitter configured to split the light beam into a reference beam and a sample illumination beam passing through the light beam guide system directed by at least one direction change mirror being pivotally actionable (TM1, TM2, TM3, TM4) to guide the reference beam and sample beam along their respective optical paths, a sample observation zone configured to receive a sample to be observed in a path of the sample illumination beam, a beam reuniter configured to reunite the reference beam and sample illumination beam after passage of the sample illumination beam through the sample observation zone, a light sensing system configured to retrieve at least phase and intensity values of the light beam downstream of the beam reuniter, and an electronic control system, the method characterized by:

receiving through a feedback loop in the control system a signal generated by the light beam from the light sensing system, generating in the control system a mirror angle control signal based at least partially on said signal received from the light sensing system, and transmitting the mirror angle control signal to said at least one pivotally actionable direction change mirror to control an angle of the pivotally actionable direction change mirror.

In an embodiment, the method comprises rotating the sample beam relative to the sample.

In an embodiment, the generated mirror angle control signal is dynamic.

In an embodiment, the mirror angle control signal is generated dynamically as a function of an angle of rotation of the sample beam relative to the sample.

In an embodiment, the generated mirror angle control signal is static.

In an embodiment, the signal received from the light sensing system and generated by the light beam on which the mirror angle control signal is based includes any one or more of intensity, coherence, fringe frequency and phase of the light beam received by the light sensing system.

In an embodiment, the method further comprises receiving a plurality of image frames data in data processing system of the microscope from the light sensing system, said plurality of image frames being generated for at least a 360° rotation of the sample illumination beam around the microscope objective optical axis.

In an embodiment, the number of frames per 360° captured by the light sensing system and data processing system is greater than 10.

In an embodiment, the image frames data are reconstituted by the data processing system, or supplied by the data processing system to a computing system, for processing into a three dimensional image of the microscopic object In an embodiment, image frames data are further employed by the data processing system, or supplied by the data processing system to a computing system, for estimating optical properties of the sample to improve the three dimensional image of the microscopic object.

In an embodiment, the method further comprises generating a three-dimensional image of the microscopic object based on the refractive index of sections of the microscopic object by determining the phase shift of the sample illumination beam after passing through the microscopic object.

Also disclosed herein is a method of controlling a microscope, the method characterized by dynamically adjusting an optical path length (OPL) of the reference beam by the control system of the microscope to keep an optical path difference (OPD) between the reference and sample beams below a coherence length of the light source, the method comprising the following steps:

a) position the rotating beam system in a first position, b) position said at least one pivotally actionable direction change mirror (TM3, TM4) configured to direct the reference beam in a first position, c) measure a position of the reference beam signal captured by the light sensing system while the sample beam is switched off, d) switch on the sample beam and measure a fringe contrast of a signal captured by the light sensing system, e) change by an increment the position of said at least one pivotally actionable direction change mirror (TM3, TM4), f) repeat steps c) to e) until the sum of increments corresponds to a pre-defined working range of the pivotally actionable direction change mirror (TM3, TM4), g) compare the fringe contrast measurements obtained for each increment and store in look-up table (LUT) of a memory of the control system the position of the pivotally actionable direction change mirror (TM3, TM4) for the fringe contrast measurement with the highest value, in conjunction with the position of the rotating beam system;

h) rotate by a small increment the rotating beam system and repeat steps b) to g) until the rotating beam system has completed a 360° rotation.

BRIEF DESCRIPTION OF THE DRAWINGS

Further objects and advantageous features of the invention will be apparent from the claims, from the detailed description, and annexed drawings, in which:

FIG. 1b is a cross-sectional view through the microscope of FIG. 1a;

FIG. 1c is a schematic simplified diagram of the configuration of a microscope according to an embodiment of this invention based on a Mach-Zehnder scheme;

FIG. 2a is a schematic simplified diagram of the configuration of a microscope according to an embodiment of this invention;

FIG. 2b is a schematic diagram similar to FIG. 2a illustrating the effect on the optical path of various defects such as manufacturing tolerances, wear, vibration or heat;

FIG. 2c shows a scanning head without defect and FIG. 2c shows a scanning head with mechanical defect (misalignment);

FIGS. 3a and 3b are partial views of samples according to first and second variants on a sample holder of a microscope according to this invention;

FIG. 4a is a view of an optical path difference (OPD) adjustment device, based on a transmissive principle, of a microscope according to an embodiment of this invention;

FIG. 4b is a simplified schematic diagram of the optical path device of FIG. 4a illustrating OPD walk-off correction;

FIG. 4c is a view similar to FIG. 4b variant illustrating OPD compensation;

FIG. 4e is are graphs showing the relation of the optical path length variation versus the angle of orientation of the transparent slabs of the OPD device of FIG. 4a;

FIG. 4i is a diagram illustrating the steps in a control procedure for adjustment of the OPD device of FIG. 4a.

FIGS. 5b, 5c, and 5d are schematic simplified diagrams of variants of the OPD device of the embodiment of FIG. 5a;

FIG. 5e is a diagram illustrating the steps in a control procedure for adjustment of the OPD device of FIG. 5a;

FIG. 5f is a diagram illustrating the steps in a control procedure for dynamic adjustment of the OPD device of FIG. 5a;

FIG. 5g is a graph illustrating the optical path length (OPL) difference of the OPD system as a function of the scanning head position allowing to determine the optimum position;

FIGS. 6a and 6b are simplified schematic views illustrating inclined illumination of a sample to be observed, FIG. 6a illustrating effect of a variation in height (Δh) of the liquid in which the sample is immersed and FIG. 6b illustrating effect of a variation in the illumination angle (α);

FIG. 6c is a simplified schematic view illustrating inclined illumination of a sample to be captured with means to correct effects of a variation in height of the liquid in which the sample is immersed;

FIG. 13 is a flowchart diagram illustrating steps of an error analysis process (P7) of a microscope according to embodiments of this invention;

FIG. 14a is a schematic illustration of a Fourier transform of the intensity pattern of a hologram captured by a light sensing system of a microscope according to embodiments of the invention;

FIG. 14b is a schematic illustration of different levels of feedback control of the tiltable mirrors of a microscope according to embodiments of this invention;

FIG. 17a is a schematic diagram of a sample illumination beam path to illustrate angles and dimensions and FIG. 17b is a table of results of the varying angles and dimensions to illustrate the effects of tolerances in fabrication, vibration or thermal effects on the angle of one or more tiltable mirrors in the sample illumination beam path needed to compensate for the tolerance.

DETAILED DESCRIPTION OF EMBODIMENTS OF THE INVENTION

Figure 1A:
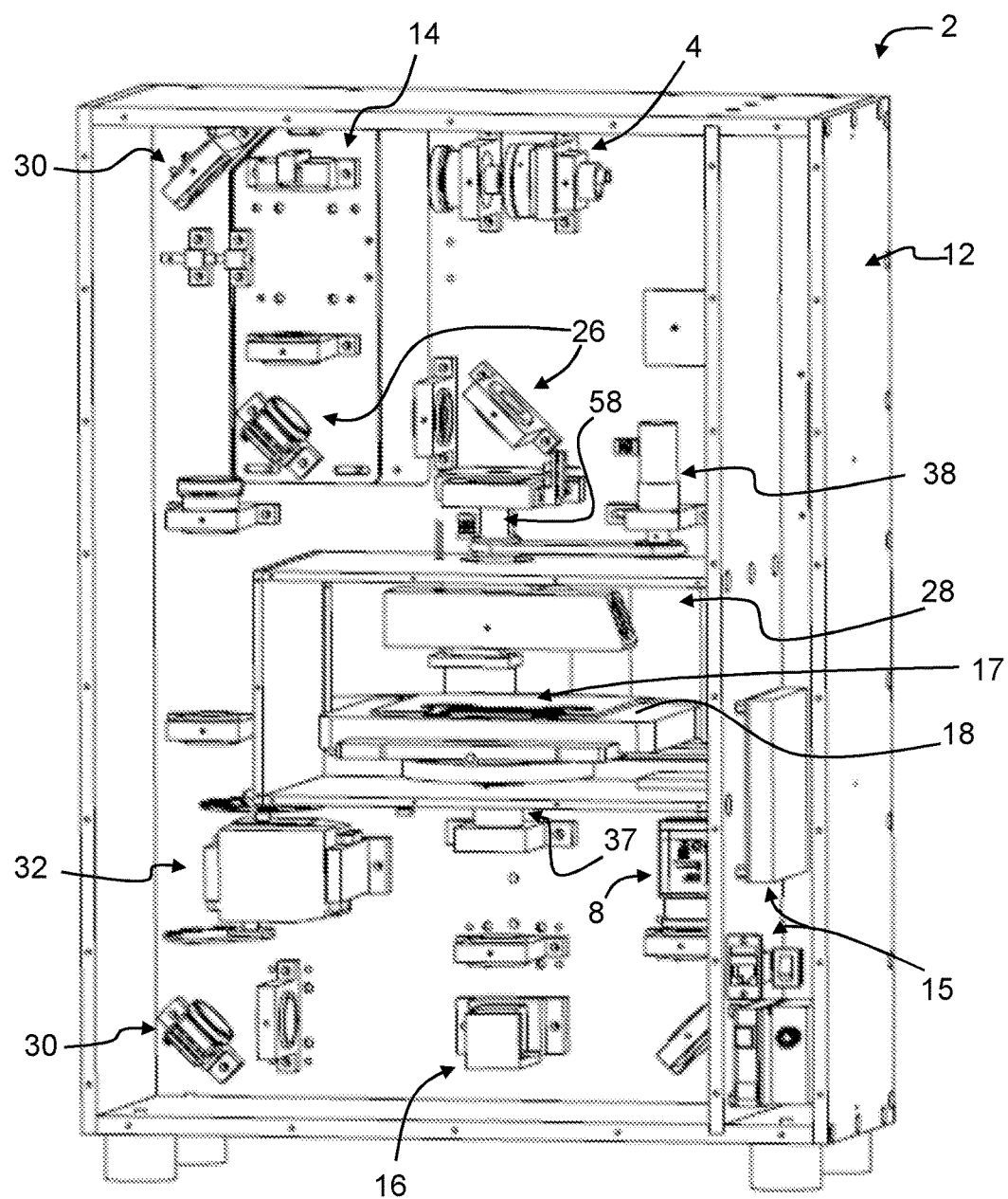
FIG. 1a is perspective view with a portion of housing removed of a microscope according to an embodiment of this invention.

Referring to the figures, starting in particular with FIGS. 1a to 2b, an exemplary embodiment of a microscope 2 comprises a light source 4 in particular a coherent light source such as a laser beam device, a light beam guide system 6, a light sensing system 8, a data processing system 10, in particular for processing generated image data, an electronic control system 15, and a housing and support structure 12 generally housing and supporting various components of the microscope 2.

The microscope 2 is capable of three-dimensional imaging of biological cells and microorganisms, including living cells. The images of cells and other samples of biological micro-matter may be generated using the techniques described in international patent application PCT/IB2011/051306 which is incorporated herein by reference.

The housing and support structure 12 comprises a sample observation zone including a sample holder 18 configured for holding biological samples in various standard and non-standard formats. The sample holder has a position adjustment mechanism allowing the position of the sample to be moved three-dimensionally, in particular a height adjustment and an adjustment in the plane traversed by the sample illumination light beam. A position adjustment mechanism for a microscope is per se well known and allows the position of the sample to be observed to be adjusted relative to the microscope objective position below (transmission) or above (reflection) the sample.

In a variant (not shown), the sample observation zone may have a conduit having a transparent section extending through the zone traversed by the sample illumination beam, configured to observe sample material supplied by flow of liquid to the illumination beam path in a closed conduit.

Referring to FIGS. 3a and 3b, biological samples may be provided in a closed containing system 3a, or in an open dish 3b (such as a petri dish). The biological samples may for instance be provided according to the following non-limitative examples. As a general requirement for any type of sample, the buffering medium 5 should not scatter incoming light. Clear liquids such as phosphate buffered saline (PBS) or 4-(2-hydroxyethyl)-1-piperazineethanesulfonic acid (HEPES) may be used for instance. In order to keep cells alive for 3 to 4 hours, samples with PBS with for instance glucose (e.g. 25 mmol) and HEPES (e.g. 10 mmol) work well. For static experiments, cells fixed with ParaFormaldeHyde (PFA) may be usable for several weeks. The observation may be made through coverslips of typically 170 microns thick (most microscope objectives are optimized for such coverslips), and due to the limited working distance of such objectives, cells should be fixed on the coverslip preferably not much further than 30 microns away from it. Optical surfaces should be as clean as possible and cells holders should be carefully cleaned, at least twice by experience, so that as few dead cells or any kind of remains as possible are floating in the mounting medium. In the example of FIG. 3a, the buffering medium 5 is sealed in a chamber to avoid liquid drying out or leakage. A seal 7, for instance in the form of a tape spacer (for instance from Grace Bio-Labs SS1X9-SecureSeal Imaging with inner diameter 9 mm and thickness 0.12 mm) is mounted between the coverslip 9 and base 11.

For living cells provided in a standard Petri dish 3b with a transparent base, the cells can be directly observed by locating the base of the Petri dish against or very close to the microscope objective 37. The amount of liquid is not important, provided that the bottom surface of the dish against which cells are located, and which forms the plane of observation 13, is covered.

The confluency of cells is preferably greater than 20% in order to ensure easy location of a cell for observation.

The coherent light source 4 may be in an exemplary embodiment a laser beam generator, for instance of the type diode laser beam at 520 nano meter wave length. Laser beams of other wave lengths may also be used being noted that the shorter of the wave length the higher the possible resolution.

The light sensing system 8 may in particular be a camera with an image sensor configured to read the light beam received after passing through the sample and transmitting the detected light signal to the data processing system 10. The camera may be of a known type with CCD, CMOS or other types of photo sensors capable of picking up the wave length, phase and intensity of the received light beam and transmitting this information to the data processing system 10.

The light beam guide system 6 is configured to divide the coherent light beam into two beams, a reference beam 7a and a sample illumination beam 7b that follow different paths, respectively a reference beam optical path 22 and a sample beam optical path 20. The light beam guide system comprises a beam splitter 14 that receives the coherent beam 7 from the coherent light source 4 and spits it into the two beams 7a, 7b. The beam splitter is per se a well known device and need not be further explained herein.

After the sample illumination beam 7b has passed through the sample 1 and before being captured by the light sensing system 8, the sample illumination beam 7b and the reference beam 7a are reunited by a beam reuniter 16. The beam reuniter, which may have the same configuration as a beam splitter operating in reverse mode is also per se well known and need not be further described herein. The splitting of the coherent beam 7 along two paths, one passing through the sample, allows measuring a phase shift of the sample illumination beam 7b relative to the reference beam 7a, dependent on the refractive index of the section of sample matter through which the sample illumination beam 7b is passing through.

The reference beam optical path system 22 comprises direction change mirrors 30 to redirect and guide the reference beam 7a along its path, and an optical path difference (OPD) adjustment device 32.

Referring to FIGS. 4a to 4c, an OPD adjustment device 32 according to the illustrated embodiment is based on a transmissive principle and comprises a first light deviating element 42 mounted on a pivot support 46, and a second light deviating element 44 mounted on a second pivot support 48. The light deviating elements 42, 44 are made of a transparent material with a refractive index greater than air, for instance a glass slab, configured to bend the reference light beam passing therethrough in a manner to allow adjustment of the length of the optical path of the reference beam. The transparent material may be made of glass or a polymer or other transparent solids, and may simply have the shape of a flat plate or slab, or may have curved or non-parallel outer surfaces. The pivot supports 46, 48 which comprise a pivot axis P1, P2 and may be coupled together mechanically by interengaging teeth 50 such that the pivot supports rotate simultaneously and in opposite angular directions w1, w2. The light deviating elements 42, 44 mounted on the pivot supports thus pivot simultaneously and in opposite angular directions to adjust the length of the optical path of the beam 7a. The greater the angle Ω between the first and second light deviating elements 42, 44, the longer the optical path of the reference beam 7a. The pivot supports 46, 48 may advantageously be micro machined parts made from a semi conducting substrate using MEMS manufacturing techniques, the rotation of the pivot supports being controlled by inductive current flowing in a section of the semi-conductor.

In an advantageous embodiment, at least one of the light deviating elements 48 may be rotatably mounted on its pivot support in order to have an additional independent rotation of angle $\Omega_1$ with respect to the other light deviating element, configured to allow adjustment for optical path misalignment (walk-off) due to misalignments, manufacturing tolerances, and the like.

In an alternative embodiment, the first and second pivot supports may be independently controlled and not mechanically directly coupled in order to allow adjustment of both optical path length and optical path walk-off.

In a variant, as schematically illustrated in FIG. 4c, at least some of the direction change mirrors 30 of the reference beam path system 20 are pivotable or tilt adjustable to adjust optical path length and/or optical path misalignment (walk-off).

Figure 4D:
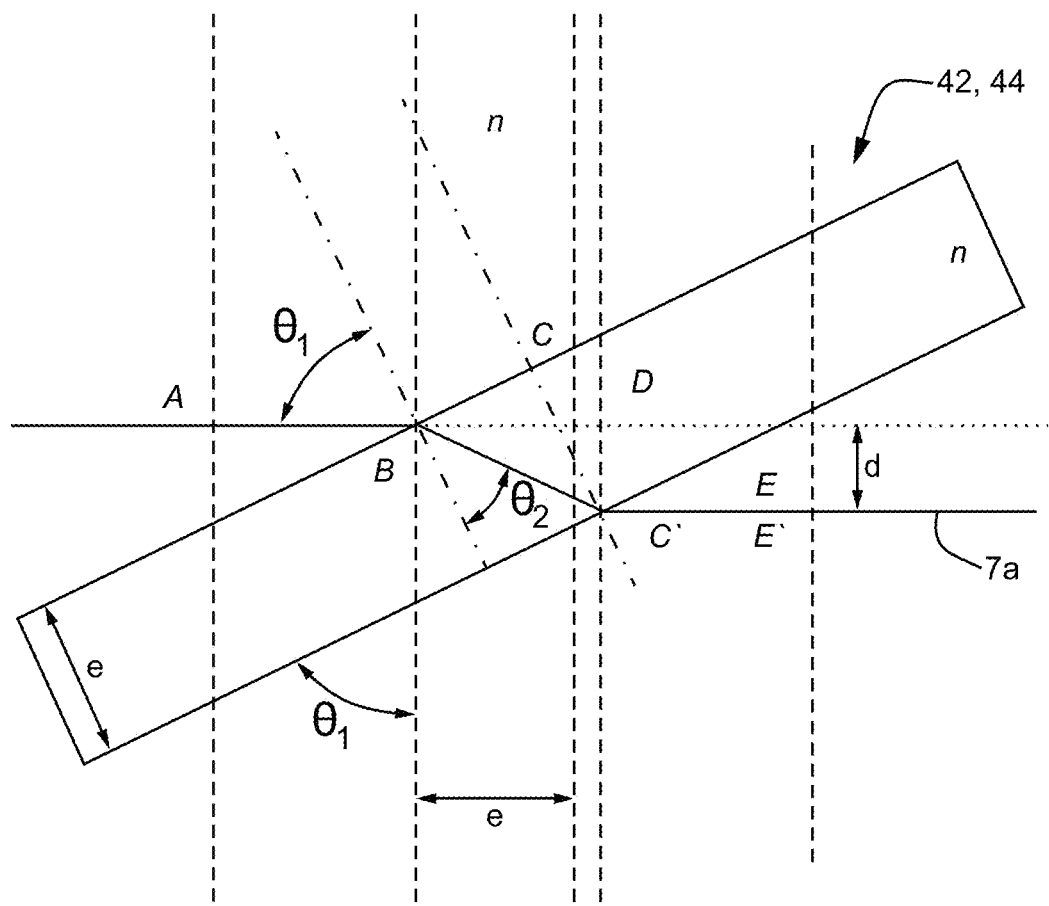
FIG. 4d is a detailed schematic view of a transparent (e.g. glass) slab of an OPD device showing various angles and dimensions discussed in the detailed description.
Figure 4E:
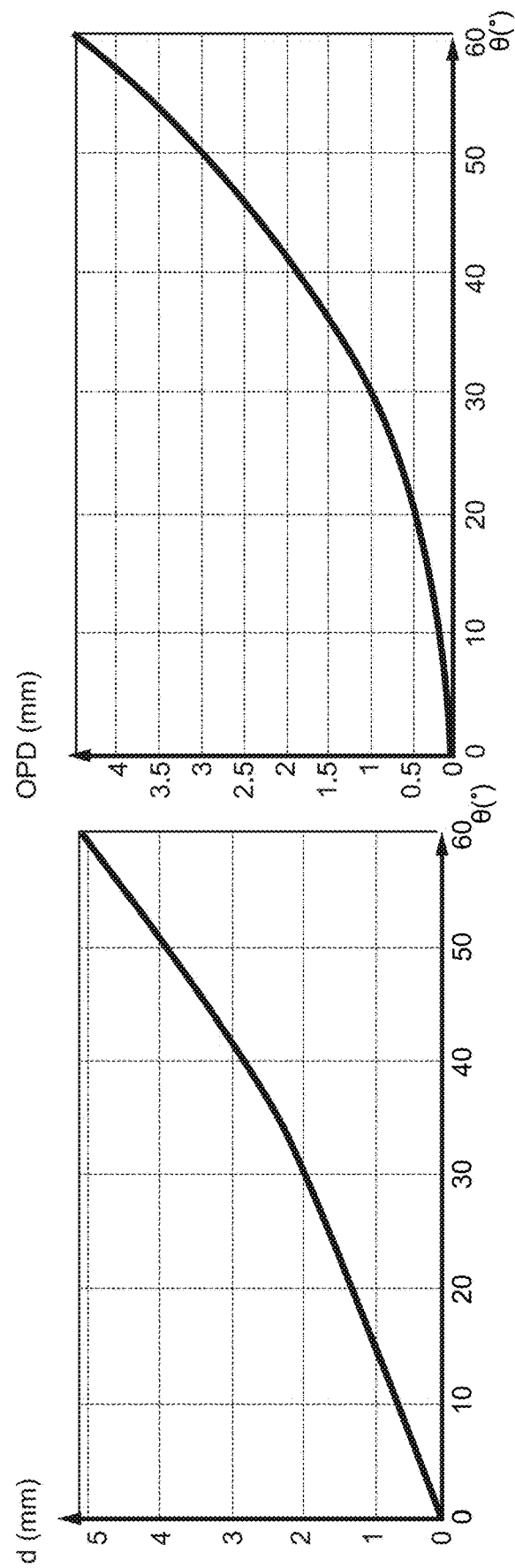

Referring to FIGS. 4d and 4e, the principle of the OPD compensation system according to the above described embodiment is further described. It is known that a glass slab may be used to laterally shift a beam and incidentally increase the optical path length. The lateral shift may however advantageously be compensated by the use of two glass slabs rotated one clockwise and the other one counterclockwise, to have both the lateral shift compensated while the OPD twice as large.

Figure 4F:
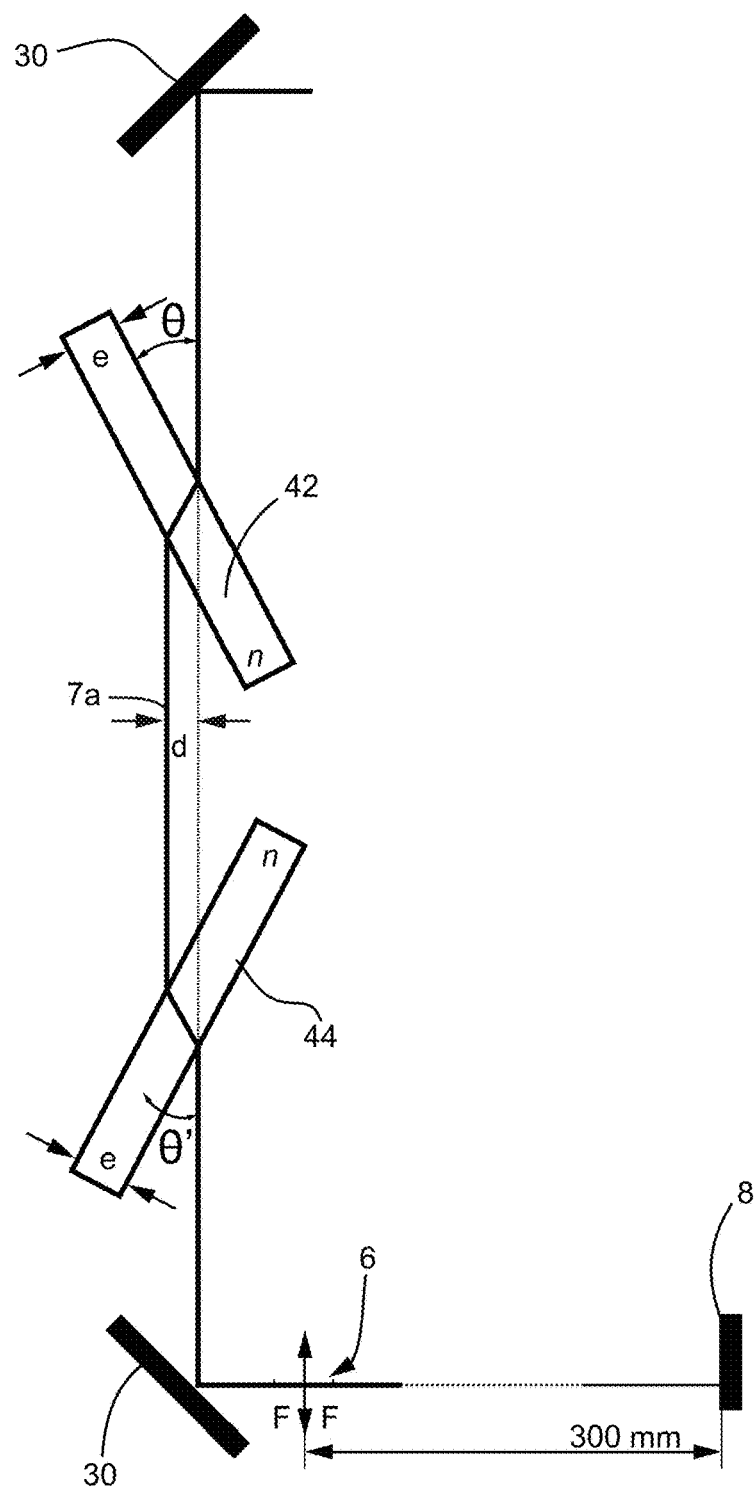
FIGS. 4f to 4h are schematic illustrations of a transmissive OPD device according to an embodiment of the invention showing perfect synchronization (FIG. 4f), imperfect synchronization (FIG. 4g) and correction of imperfect synchronization by means of tiltable mirrors (FIG. 4h)

Referring to FIGS. 4d to 4f, the lateral shift (C'D) and the OPD namely, OPD=(BC'−BC), can be expressed as follows:

$$\overline{C'D} = e \cdot \sin\theta_1 \left(1 - \frac{\cos\theta_1}{\sqrt{n^2 - \sin^2\theta_1}}\right)$$

$$OPD = ne\left(\frac{1}{\cos\theta_2} - 1\right) - e \cdot \left(\frac{\cos\theta_1 - \theta_2}{\cos\theta_2} - 1\right)$$

To compensate the lateral shift of the beam, another glass slab is tilted by the opposite angle: the shift is compensated and the OPD is doubled at the same time as illustrated in FIG. 4f. FIG. 4f shows the OPD compensation results according to the above calculation for two slabs of 10 mm thick each, of RI 1.5 and tiltable from 0 to 60°.

Figure 4G:
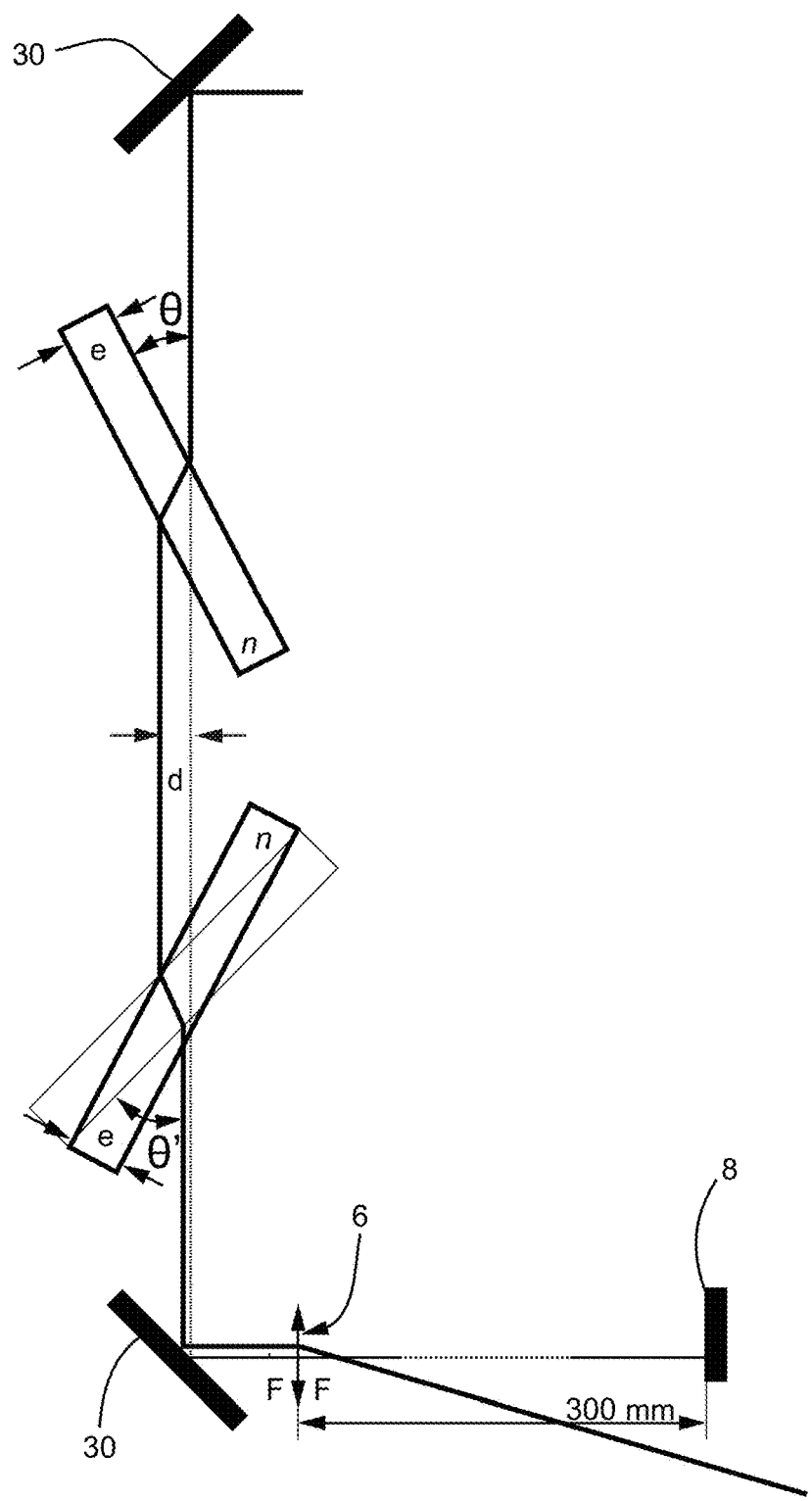
Figure 4H:
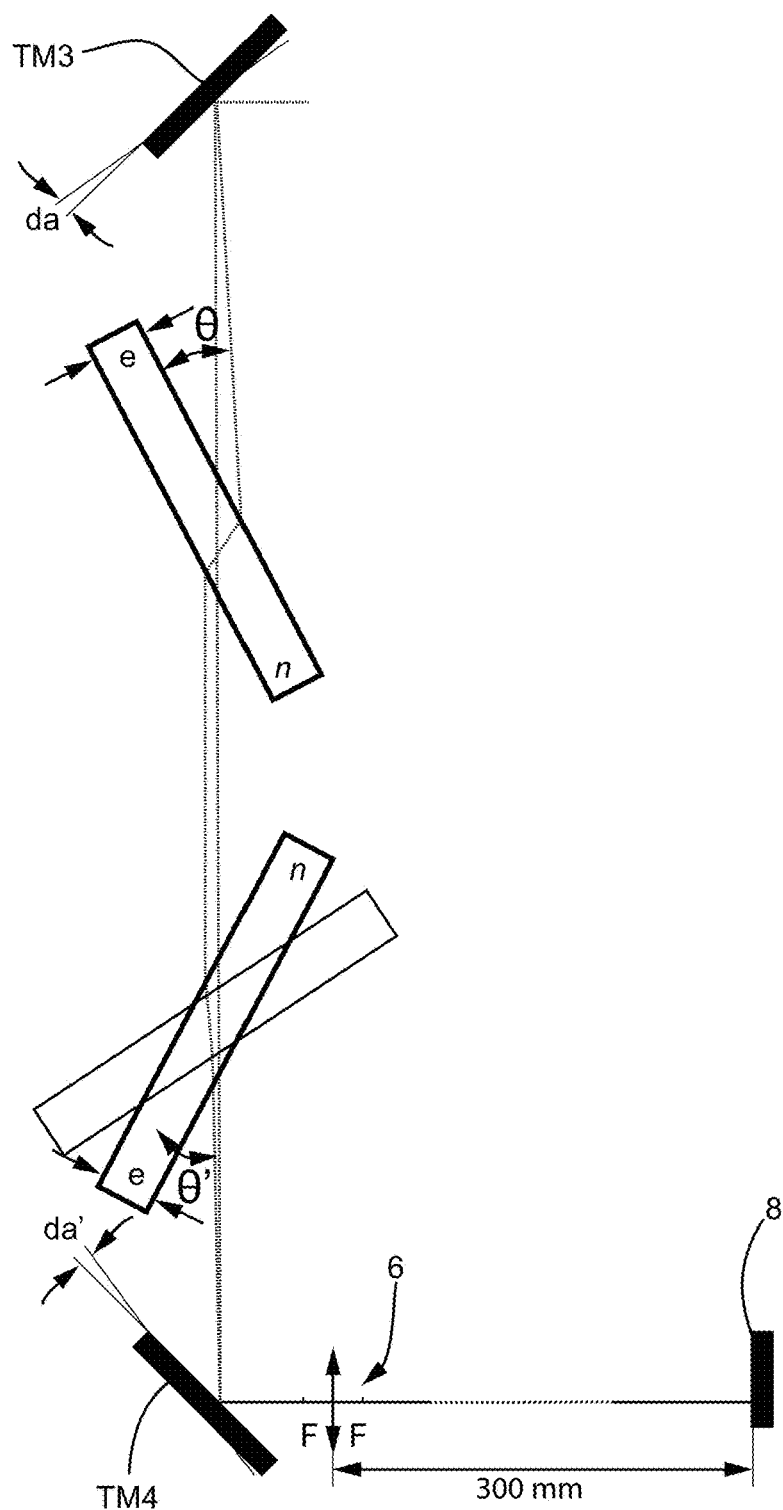
Figure 4I:
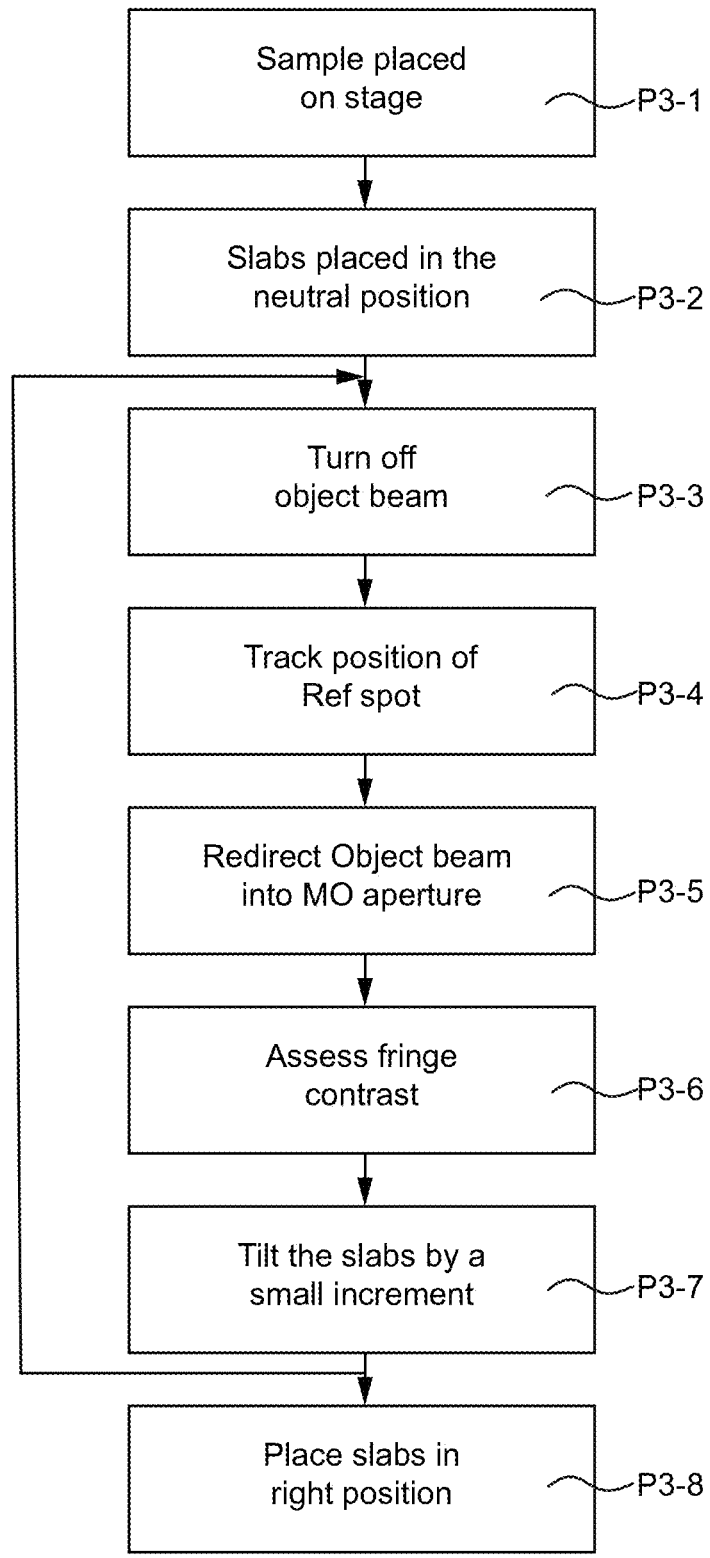

The OPD adjustment device according this embodiment may be implemented into the microscope to adapt the optical path to the sample thickness between two mirrors 30 as shown in FIG. 4g. Due to an error of command, a difference of glass slab thickness e, or simply loose tolerance in the assembly of components in the support structure 12, the exiting reference beam 7a will be laterally shifted as shown in FIG. 4h. For a distance of 300 mm between the lens and the camera and a focal length of 20 mm for the lens, if one admits a possible shift of a tenth of the field of view on the sensor, i.e. around 500 µm, it means a maximum admissible lateral shift of about 40 µm on the second mirror. If we admit such a maximum lateral shift, the two slabs 42, 44 should be tilted by angles with a maximum difference of 0.25°, or the differences of thicknesses of the slabs should not exceed 100 µm. To avoid imposing tight tolerances on the mechanical drives or the dimensions of the glass slabs, it is advantageous to replace the mirrors 30 by tiltable mirrors TM3, TM4 controlled by a microcontroller of the control system 15—see FIG. 4i.

The procedure of command of the full OPD compensation system can be described as follows with reference to FIGS. 4j and 4h:

A sample 1 is placed in the sample observation zone 17 and ready to be explored;

The glass slabs 42, 44 are placed in the neutral position (θ=90° in FIG. 4h).

The tiltable mirrors TM3, TM4 (for instance MEMS mirrors) are controlled to best uniform the intensity on the sensor. To ease the search, the sample illumination beam 7b can be deflected out of the aperture of the microscope objective 37;

The fringe contrast is evaluated from the calculation of the carrier peak energy compared to the DC component energy in the Fourier domain.

The OPD scanning starts by tilting the glass slabs 42, 44 in a certain direction by a certain small angle;

For each increment of angle (the slabs can be driven by a stepper motor with an appropriate gear reduction ratio), the laser spot is kept centered on the light sensor through a PID algorithm;

The sample illumination beam 7b is redirected properly and the fringe contrast is assessed;

Once the scan is complete, the slabs 42, 44 are properly oriented in the position which yield the highest fringe contrast.

The positions of the tiltable mirrors TM3, TM4 are refined.

The microscope is ready to optimally measure the sample 1.

In a variant, to speed up the iterative search described above, the optical thickness obtained from procedure P1 (used in procedure P2) can be used to define a starting point of the slab angles close to the expected optimal position: the tilt angle of the slabs resulting in the highest fringe contrast is directly dependent on the optical thickness of the sample estimated in procedure P1.

Referring to FIGS. 5a to 5d, an OPD adjustment device 32 according to the illustrated embodiment is based on a reflective principle and comprises a first direction change mirror 30a, a second direction change mirror 30b, and a third direction change mirror 30c. At least one of the first and third direction change mirrors 30a, 30c are tiltable, whereas the second direction change mirror 30b, which is positioned intermediate the first and third mirrors along the optical path of the reference beam, is translatable. Translation of the second mirror 30b changes the length of the optical path, the tiltable first and third mirrors 30a, 30c being rotated to correct the direction of the reference beam as a function of the displacement of the second mirror 30b.

Figure 5A:
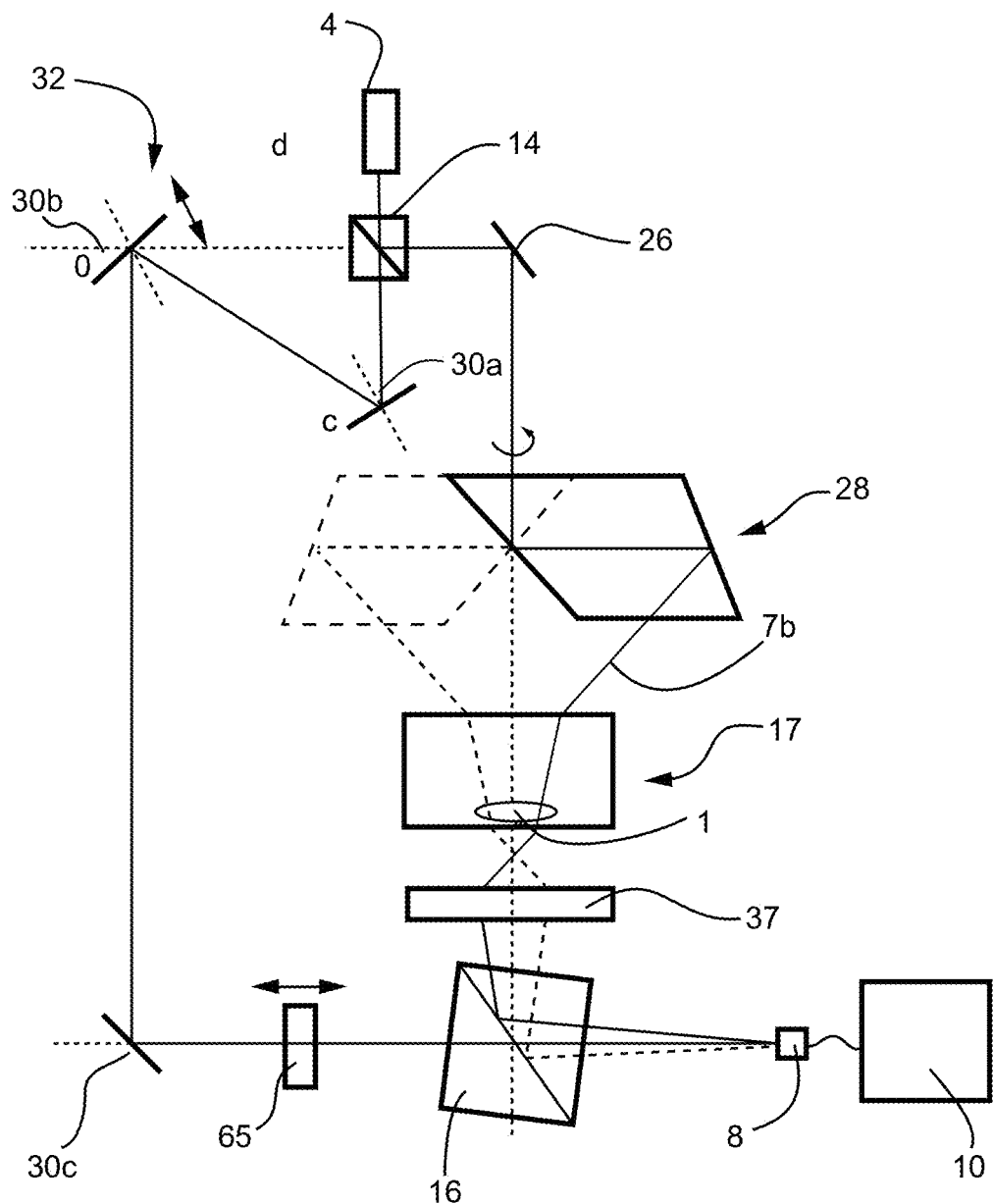
FIG. 5a is a schematic simplified diagram of the configuration of a microscope comprising an OPD device based on a reflective principle, according to an embodiment of this invention.
Figure 5B:
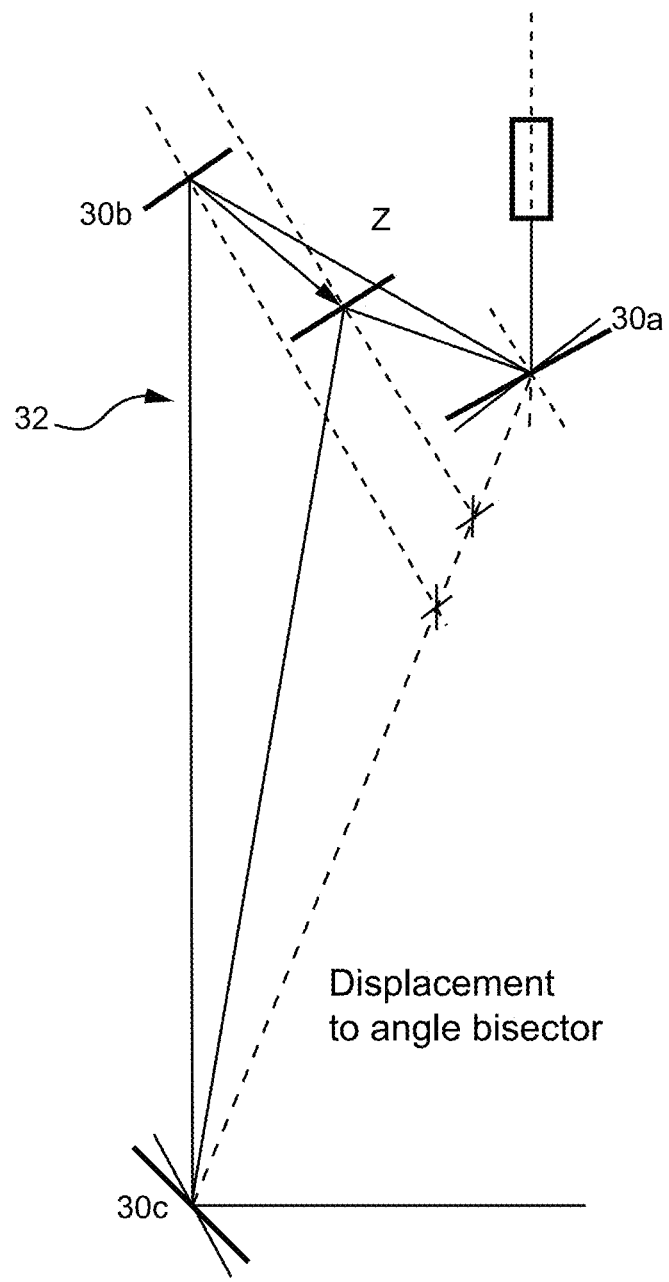
Figure 5C:
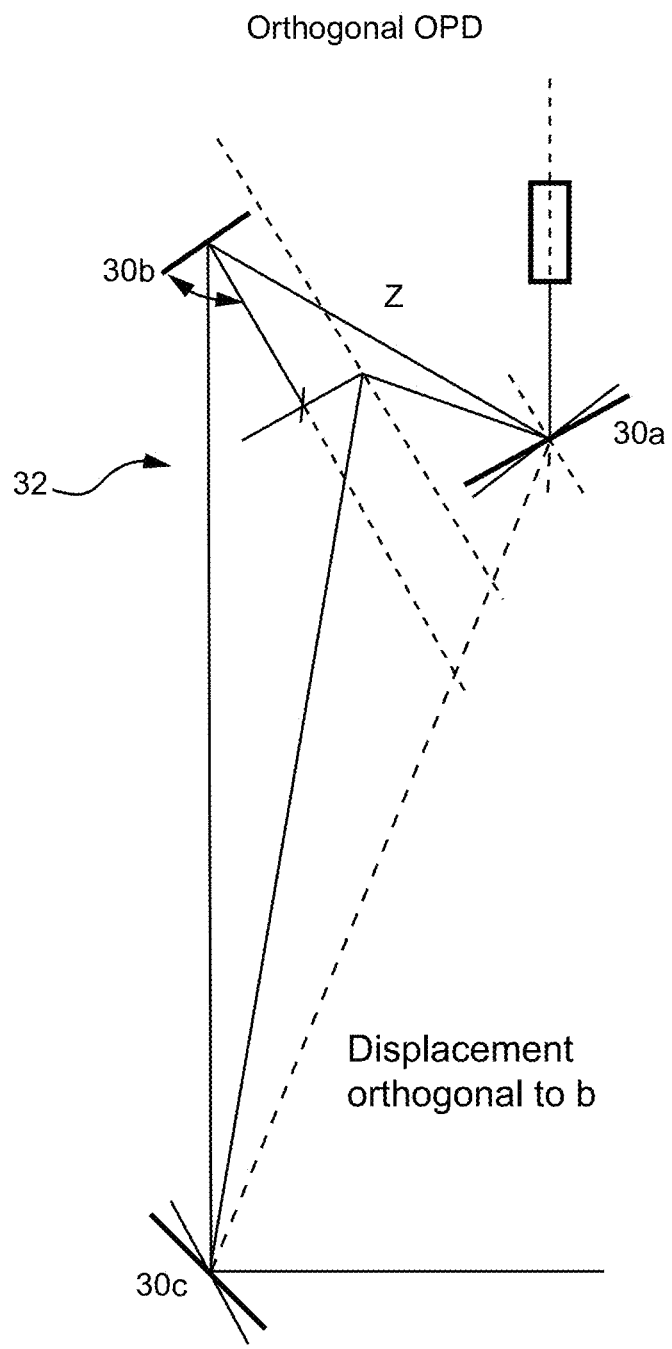
Figure 5D:
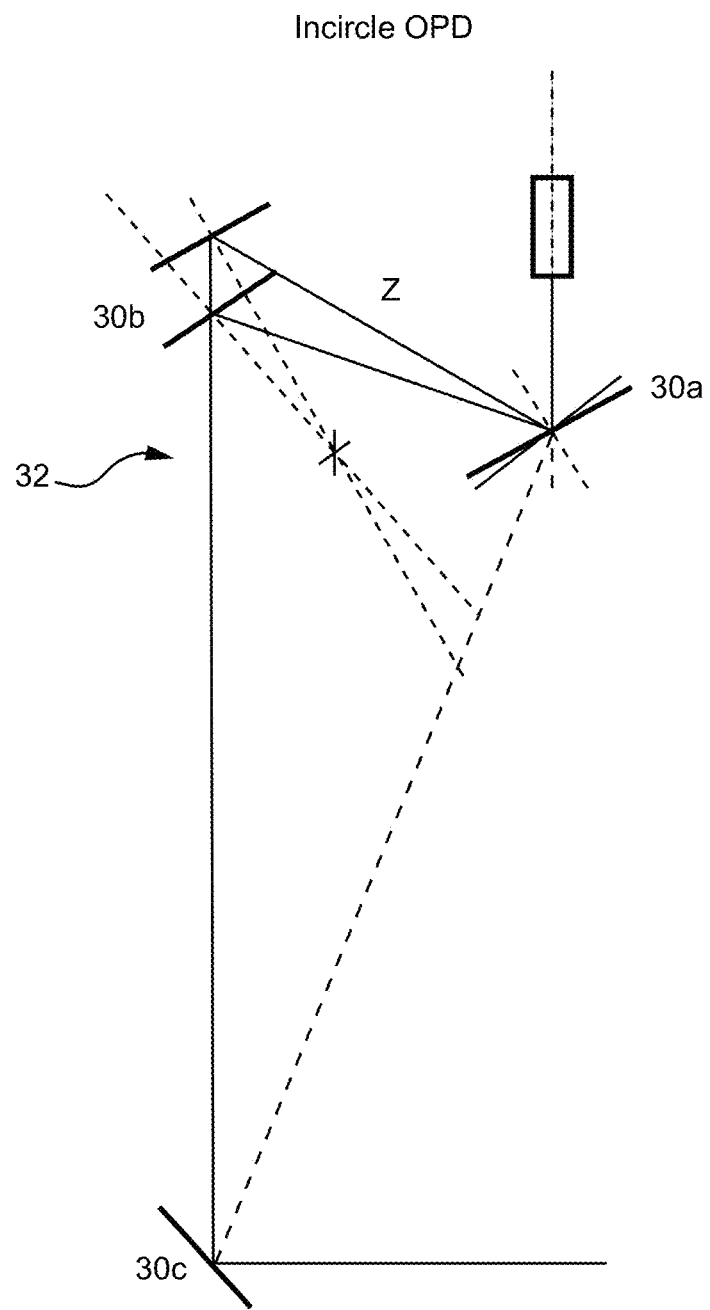

In the variant of FIG. 5b, the second mirror is mounted on a support (not shown) configured to move the second mirror in a direction oblique to a direction orthogonal to the second mirror reflection plane (also named angle bisector displacement), whereby both first and third mirrors 30a, 30b are tiltable to adjust for the variation in angle of the reference light beam. In the variant of FIG. 5c, the second mirror is mounted on a support (not shown) configured to move the second mirror orthogonally to the second mirror reflection plane, whereby both first and third mirrors 30a, 30b are tiltable to adjust for the variation in angle of the reference light beam. In the variant of FIG. 5d, the second mirror is mounted on a support (not shown) configured to move the second mirror in a direction parallel to the reference beam reflected off the second mirror (also named incircle displacement), whereby the first mirror 30a is tiltable to adjust for the variation in angle of the reference light beam, and the second and/or third mirrors are optionally tiltable.

An advantage of the reflective OPD embodiment compared to the transmissive OPD embodiment is to minimize the error inducing effects of optical surfaces such as intensity variations or astigmatism, and to use the degrees of liberty readily available in MEMS tilting mirror motions. Procedure P4 may be essentially equivalent to that of procedure P3, replacing slab rotation with mirror translation.

Referring mainly to FIGS. 1a to 2b, the sample beam optical path system 20 also comprises direction change mirrors 26 in order to guide the sample illumination beam along its chosen path. The sample beam optical path system further comprises a sample illumination device 28 comprising a mirror system 34 and a rotating mechanism 36. The mirror system 34 comprises a first mirror 54 and a second mirror 56 configured to direct the sample illumination beam 7b at a pre-determined angle α, with respect to the axis A of the microscope objective 37, towards the sample 1.

In an embodiment, the rotating mechanism 36 comprises a motor drive 38 and a rotating support 40 the mirror system 34 being mounted in the rotating support 40. In the present exemplary embodiment, the drive 38 is coupled to the rotating support via a transmission comprising a belt 39, however, many other transmission systems could be used to couple the drive to the rotating support such as a gear system, or by magnetic induction coupling.

The rotating support 40 comprises a hollow or tubular axis 58 configured to allow the sample illumination light beam to pass therethrough, and a mirror support body 60 in which the first and second mirrors 54, 56 are mounted. The rotating support 40, in particular the hollow axis 58 is mounted via bearings 59 to the housing support structure 12.

Figure 8:
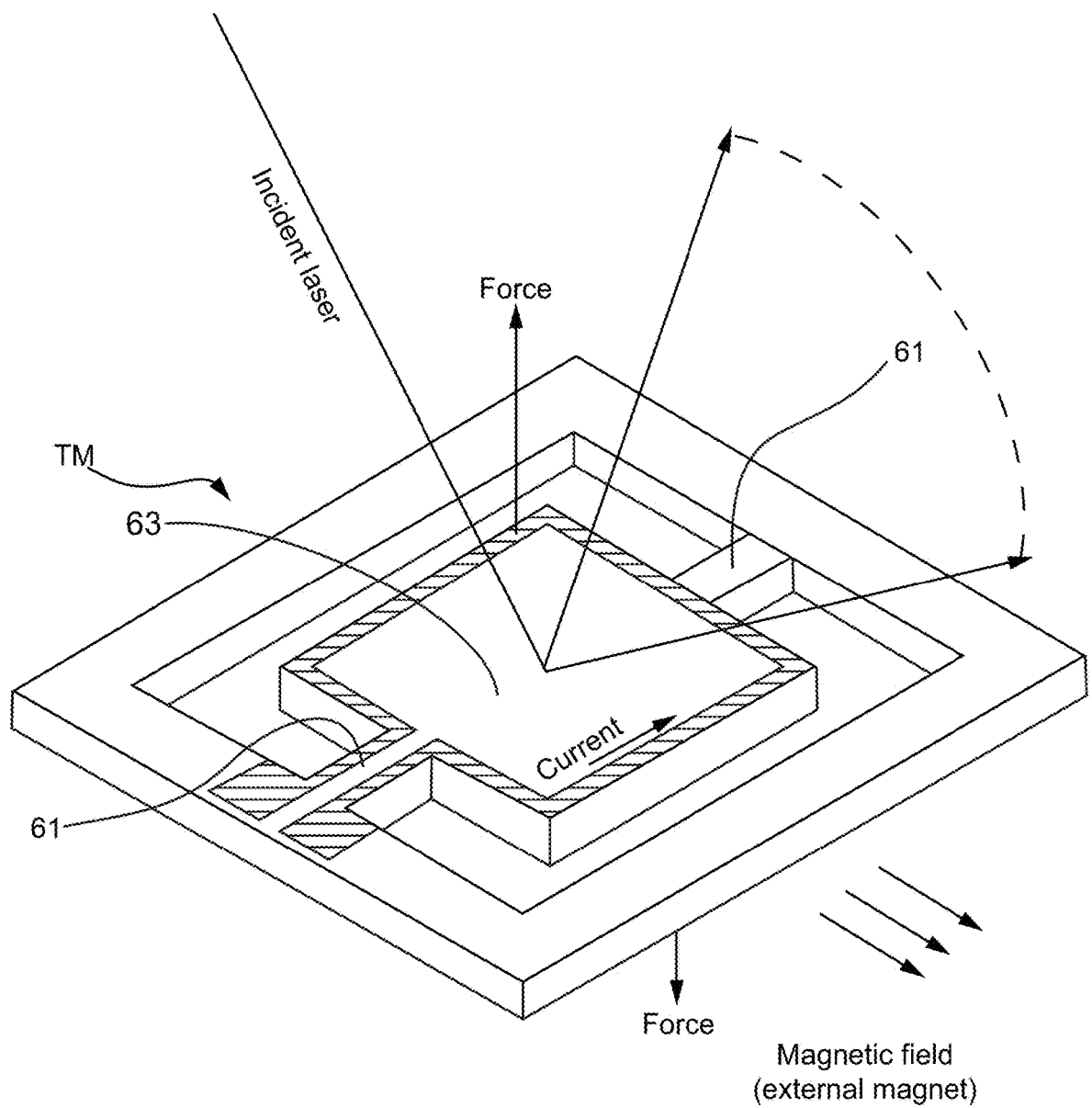
FIG. 8 is a perspective simplified view of a MEMS based mirror with adjustable tilt angle for use in the microscope according to embodiments of this invention.

The first mirror 54 redirects the light beam projected through the hollow axis onto the second mirror 56, and the second mirror redirects the light beam onto the sample 1 positioned on the sample holder 18 at an illumination angle α. The first and second mirrors may be arranged in a fixed relation within the mirror support body 60. In other variants, either the first mirror or the second mirror, or both, may be pivotally adjustable. The pivotally adjustable first and/or second mirrors may be useful to adjust the illumination angle to a chosen illumination angle, and/or to adjust for misalignment due to manufacturing tolerances, or due to disadjustments during transport and handling or through use. The illumination angle may also be adjusted by adjusting the angle of the direction change mirrors 26a, 26b of the sample beam optical path system 20. The angle adjustable mirrors 26a, 26b, can be micro machined parts in a form of MEMS fabricated mirrors formed out of semi-conducting material as illustrated in FIG. 8, as is per se known in the art, to form mirrors with tilt angles that are electronically adjustable. The electronically angle adjustable mirrors thus allow to compensate for manufacturing tolerances to calibrate the device, and to adjust illumination angles to chosen values either dynamically or statically as needed. Auto calibration of the microscope is thus possible after manufacturing and before each use to correct for any misalignments, production tolerances, thermal effects, and wear that deviate the beam 7b' from the chosen path 7b as best illustrated in FIG. 2b.

The angle adjustable mirrors in the sample illumination path system may advantageously also enable static or dynamic adjustment for the refractive properties of the sample. For instance, a change in the height delta h of the liquid (see FIGS. 5a to 5c) within which the sample is immersed may be corrected for. Dynamic correction may be applied to compensate for a non-uniform thickness of the liquid medium in which the sample is immersed with respect to the path of the light beam as the beam rotates through 360° around the microscope objective optical axis A. This non-uniform thickness may be due to a non-horizontal mounting of the sample container, or due to the presence of meniscus of the liquid due to surface tension.

A closed loop regulation system for automatically controlling the tilt angle of the mirrors 26a, 26b based on feedback signals from the light sensing system 8 may be incorporated in an electronic control circuit of the control system 15 of the microscope. The electronic control circuit may also control the rotating beam mechanism 36 and the light source 4.

Figure 1B:
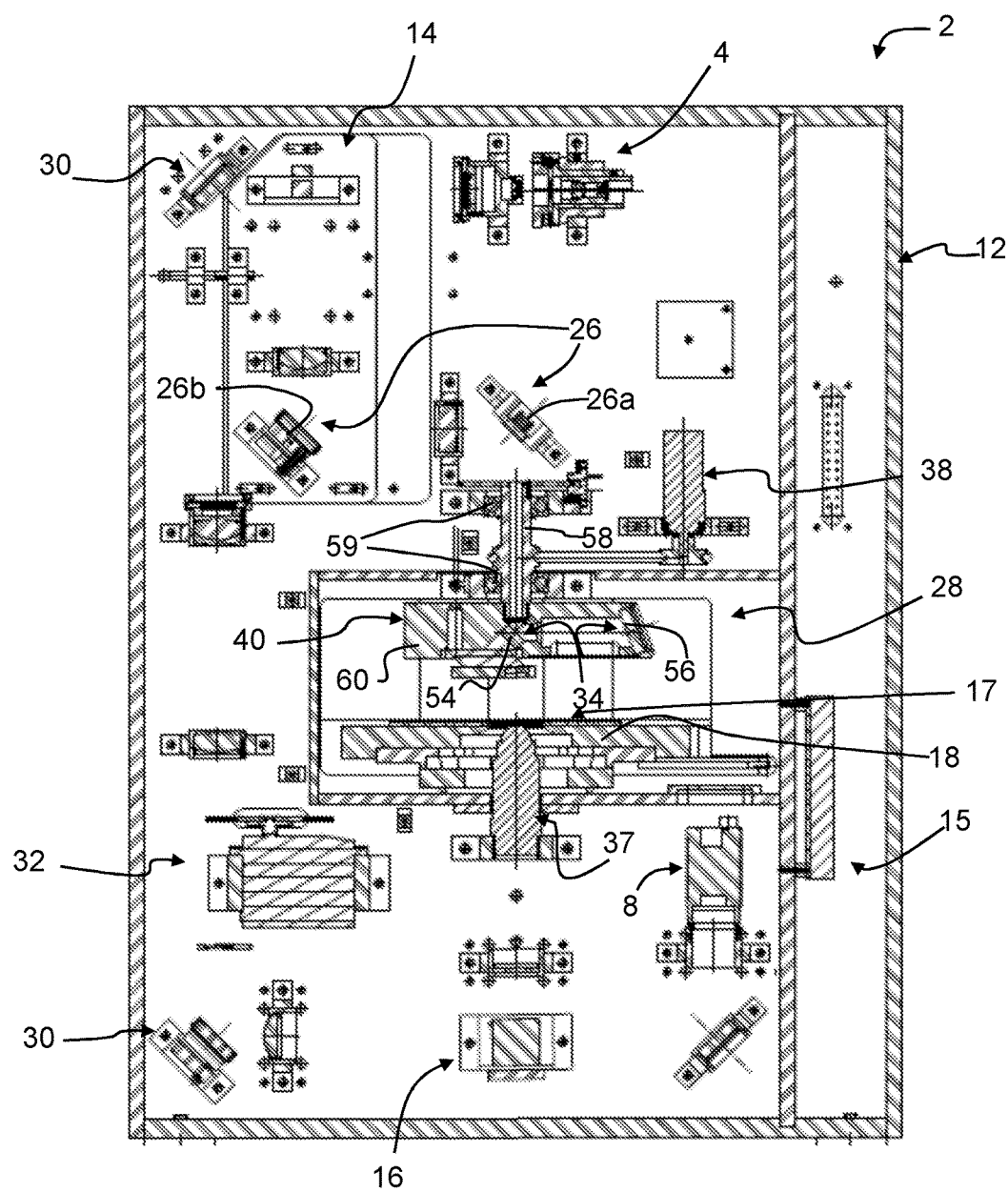
Figure 1D:
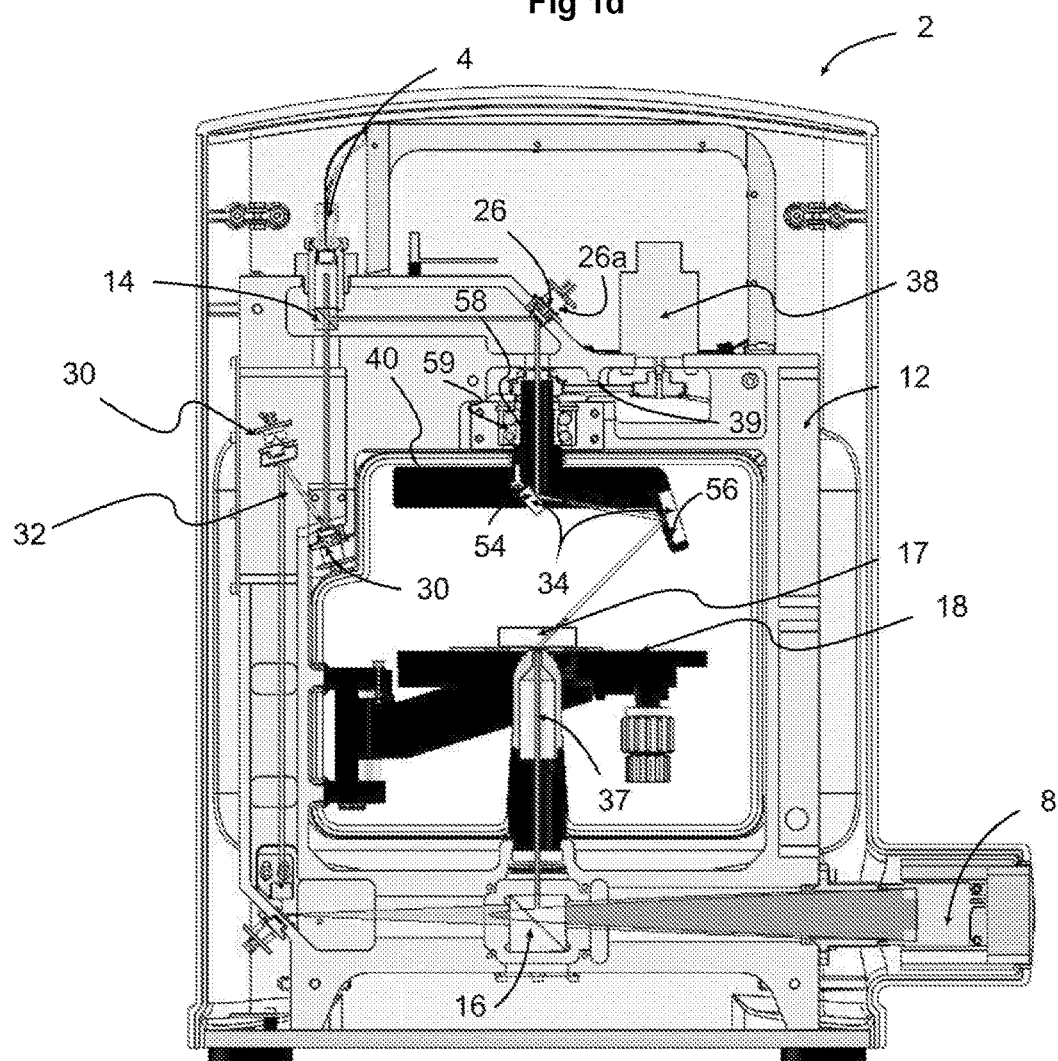
FIG. 1d is cross-sectional view of a microscope according to another embodiment of this invention.
Figure 1E:
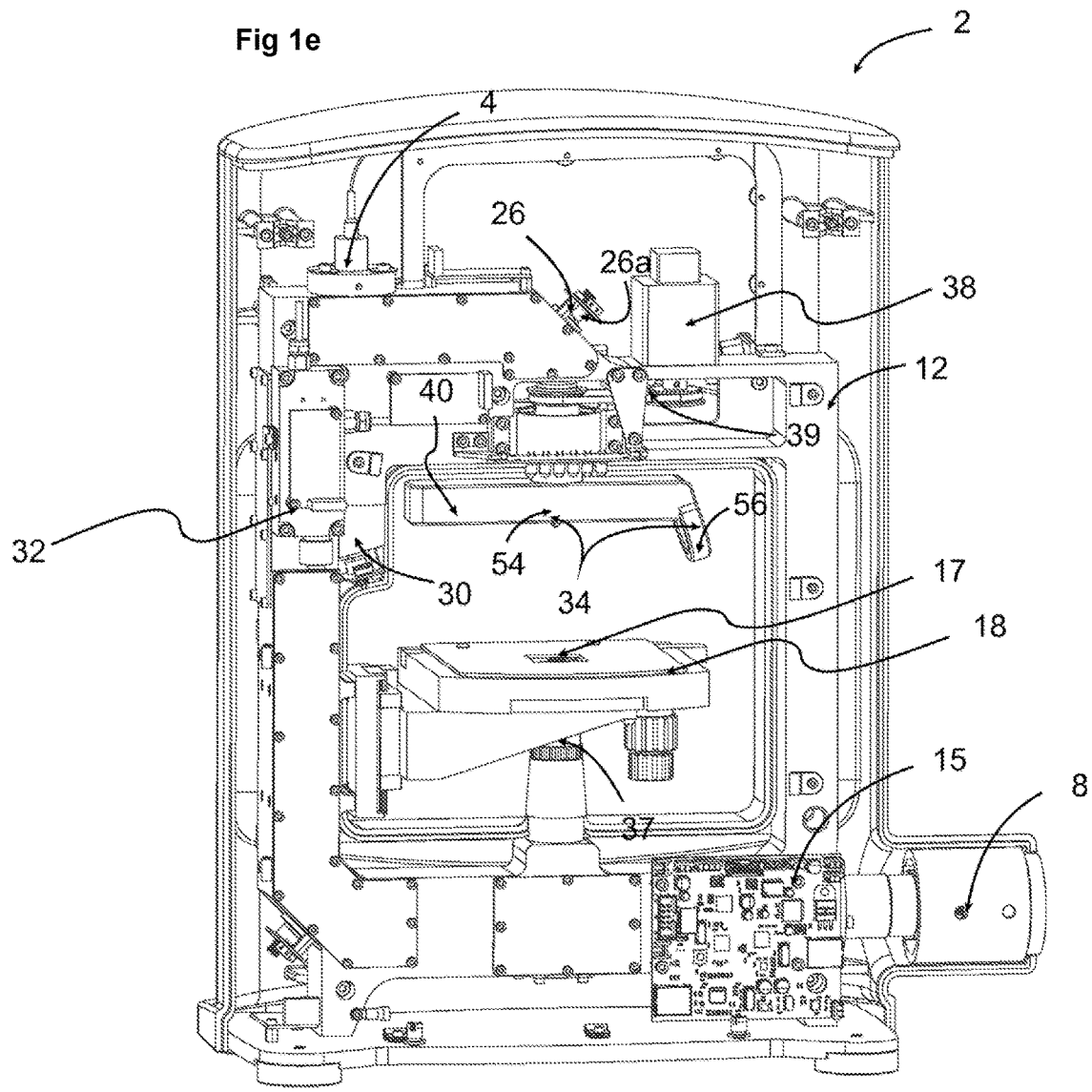
FIG. 1e is a cross-sectional perspective view of the microscope of FIG. 1d.
Figure 2C:
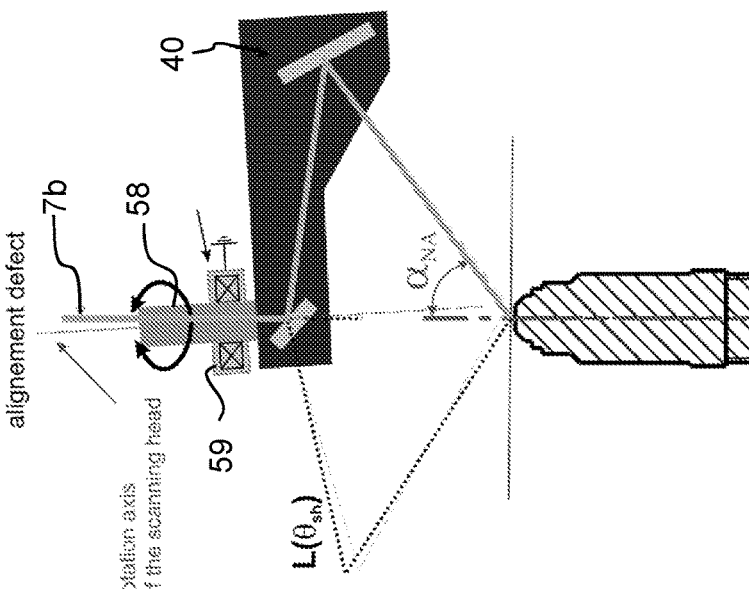
FIGS. 2c and 2d are schematic diagrams of the configuration of a part of the microscope illustrating the effect of a mechanical defect on the optical path length during a revolution of a rotating scanning arm of the microscope, whereby
Figure 2D:
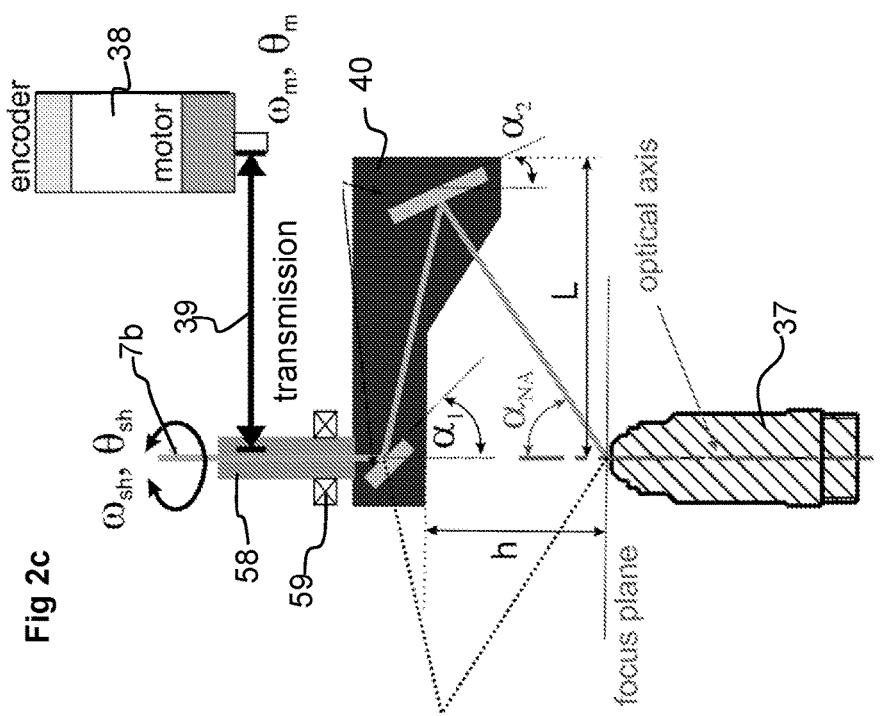

In the embodiment illustrated in FIG. 1b, the rotating support allows to rotate the sample illumination beam during an image capture 360° while maintaining a fixed illumination angle α. During the rotation of the mirror system 34, a chosen number of image frames may be captured by the camera, for instance in a range between 20 and 200 image frames, for instance around 100 image frames, each representing a different view angle of the microscopic object being observed. Each frame represents a two-dimensional image section representing the refractive index distribution in a planar section of the sample being observed. The two dimensional sections may be compiled to reconstitute a three-dimensional refractive index based image of the observed microscopic object. The rotation speed of the beam, which depends on the rotational speed of the rotating support 40 as concerns the embodiment illustrated in FIG. 1b, may be adjusted as a function of the frame capture frequency of the light sensing system 8.

The rotating sample illumination beam with a pre-determined illumination angle α according to the invention is particularly advantageous over conventional solutions based on lenses, in that it allows to illuminate the microscopic object at a large illumination angle α, as large as the numerical aperture (NA) of the microscope objective 37 allows. This provides much greater flexibility in the size of the samples that may be positioned on the sample holder and viewed by the microscope while significantly reducing the manufacturing costs of the microscope and sensitivity to the quality of the optical elements along the optical path.

Moreover, the rotating mirror system does not change the beam shape as opposed to lenses or refractive or diffractive elements which thus need to be manufactured with extremely high quality in order to reduce beam shaping. The latter significantly increases production costs as opposed to the solution provided by the present invention. In the present invention the illumination angle α may be changed, either by replacing the rotating support 40 if the mirrors are in a fixed relationship therein, or by having rotatable first 54 and/or second 56 mirrors in the rotating support whereby the illumination angle limit is determined by the numerical aperture of the microscope lens. For example, for a numerical aperture of 0.8, the illumination angle may be 55°, and with a numerical aperture 1.3 the illumination angle may be up to 64°. The higher the angle, the greater the sensitivity and thus the resolution of the two-dimensional phase image and thus the three-dimensional phase image reconstituted therefrom.

The tilt adjustable mirrors in the optical path of the sample illumination beam are particularly advantageous in that they allow to adjust for misalignments, manufacturing tolerances, wear during life of the device, and also for correction, either static or dynamic, for the variations such as the height of the liquid in which the matter to be observed is immersed.

Another particularly advantageous feature of the invention is the optical path difference (OPD) adjustment device 32 having tilt adjustable transmissive or reflective light deviating elements 42, 44, 30a, 30b, 30c that allow for automatic and continuous calibration or adjustment of the optical path difference and also to correct for OPD walk-off without having to change the elements. In conventional devices, a series of transparent discs of different thicknesses are positioned in the reference beam path as a function of the adjustment of the optical path, however this does not allow a continuous and fine adjustment, nor does this allow to correct for OPD walk-off.

Figure 7A:
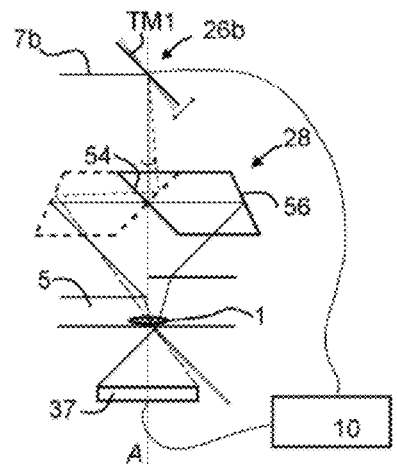
FIGS. 7a, 7b, 7c and 7d are simplified schematic illustrations of a rotating illumination beam system relative to a sample according to different variants of a microscope according to this invention.
Figure 7B:
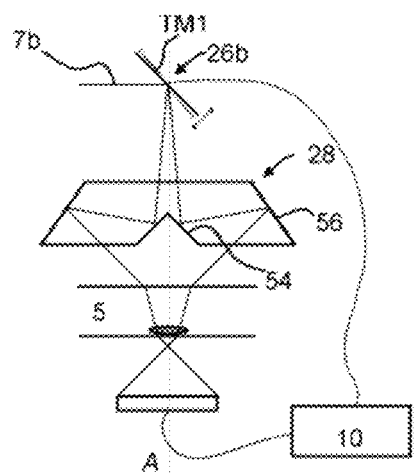
Figure 7C:
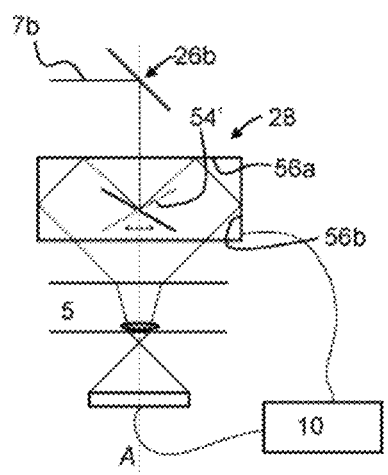

Referring to FIGS. 7a to 7c, starting first with FIG. 7a, in a first variant the rotating beam mechanism 36 comprises the mirror system 34 with first and second mirrors 54, 56, is mounted in a support 40 that is rotatably mounted on the housing support 12 and that is rotated through 360° around the microscope objective optical axis A to perform the image capture of the sample 1. The second direction change mirror 26b may be adjustable, according to a variant, or fixed, whereby in the adjustable variant the angle of illumination a of the beam may be varied either to change the illumination angle, or to maintain a fixed illumination angle and correct for any misalignment or misadjustment. In the second variant of FIG. 7b, the mirror system 34 of the sample illumination device is fixed, the first mirror 54 being essentially in the form of a central cone that redirects the beam 7b to the second mirror 56 also forming essentially an outer conical ring. The beam rotation is performed by the second direction change mirror 26b of the sample beam optical path system 20, the mirror performing a continuously tilting circular movement in order to rotate the illumination beam around the cone formed by the first mirror 54 such that the illumination beam rotates 360° around the microscope objective optical axis A. The advantage of this solution is the limited mechanical parts, however with a greater sensitivity to the accuracy of curvature of the conical mirror surfaces as compared to the mechanical solution illustrated in FIG. 7a.

FIG. 7c also illustrates a system with a fixed support 40 whereby the rotating illumination beam is actuated by a central tiltable mirror 54' that performs a circular tilting movement through 360° and that reflects the beam towards an upper first mirror 56a that reflects to a second lateral mirror 56b.

Figure 7D:
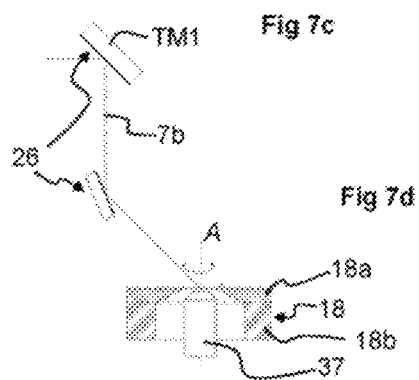

FIG. 7d illustrates an embodiment in which the sample holder 18 comprises a base 18b and a rotating sample support surface 18a on which the sample is placed. The sample illumination beam 7b in this embodiment is thus rotated relative to the sample by rotation of the sample holder about the optical axis A of the microscope objective 37 while the beam remains in a fixed angular position. Either one or both of the direction change mirrors 26 may be a pivotally actionable mirror TM1, for instance in the form of a MEMS component.

Sample Illumination Procedure P1—Example of an Autocalibration Routine:

According to an embodiment of the present invention, the microscope may advantageously comprise an electronic control system and software configured to implement an autocalibration routine with the aim of controlling the detection angle of a tiltable (e.g. MEMS) mirror 26, TM1 with the aim of correcting for geometric misalignment so that the sample illumination beam 7b impinges upon a focal plane of the microscope objective 37 in the center of its field of view (FOV). This is equivalent to the incident light spot being centered on a sensor surface of the camera 8, respectively being centered on the captured digital image. The corrections are dynamic in the sense that they may change with the rotation angle of the sample rotating beam system 36.

As the misalignments for which one would like to correct are identical for each rotation of the rotating beam system 36, the signal controlling the tiltable mirror 26a is periodic with respect to the system's rotation. For each degree of freedom i=x,y in the tiltable mirror, the signal can be described using a countable number of discrete Fourier sine and cosine coefficients $a_n^i$ and $b_n^i$, respectively, corresponding to the rotating beam system's rotation frequency $f_0$ and integer multiples $nf_0$ thereof. Due to the rotational character of the optical configuration, the dominant Fourier coefficients are the DC terms $b_0^i$, and those related to the fundamental frequency, $a_1^i$ and $b_1^i$, corresponding to an angular offset and a circular angular motion of the mirror with the same frequency as the rotating beam mechanism, respectively. While higher order terms may be necessary to fully describe the required correction signal, in most cases only a handful (approx. 10) of terms is required and thus presents a memory-efficient means for storing the correction information—one which, for example, can easily be stored in the limited memory of a microcontroller performing the real-time correction during operation.

If the incident light spot is in the objective's field of view (FOV), the spot's position can be determined quantitatively by summing the pixel values in the camera image's four quadrants. Taking the difference between the sums of two diagonally opposite quadrants then yields two values u, v that describe the spot's position with respect to the image center. A spot in the center of the FOV will yield u=v=0.

The values u, v can be used as a feedback value, e.g. for a PID control. The correction signal trajectory can then be obtained by rotating the sample illumination beam relative to the sample and using the PID to keep the spot in the center of camera's digital image. However, this process may lead to the following difficulties: (i) in general, the spot is initially not in the camera's field of view and so the feedback loop is broken; and (ii) as the PID control's speed is limited by the camera's frame rate, it may require very large frame rates to be able to follow the spot during rotation. In other words, during rotation, it can happen that the spot completely leaves the camera's field of view between two camera frames, preventing the PID from being able to react.

Figure 9:
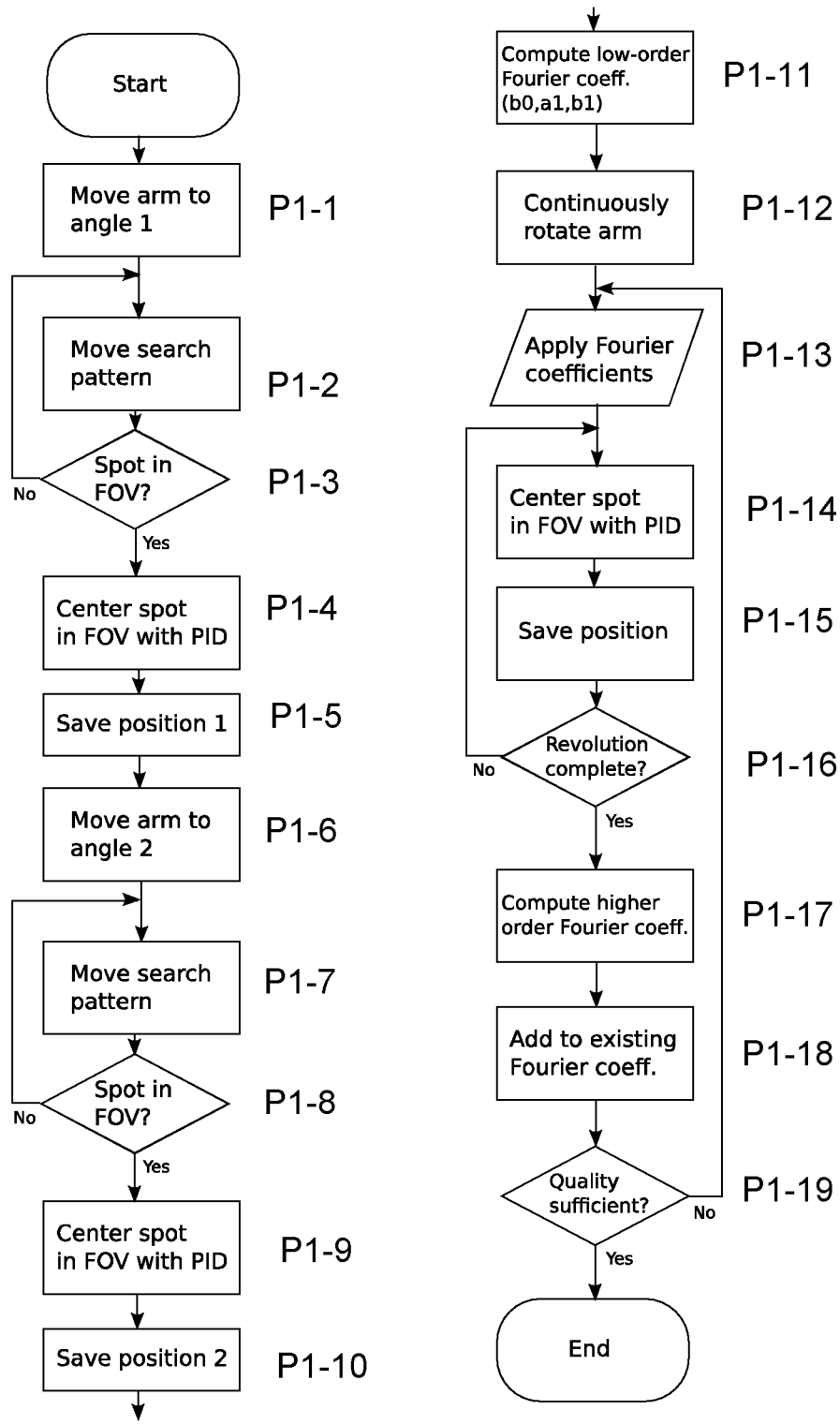
FIG. 9 is a flowchart diagram illustrating steps of a calibration process (P1) of a microscope according to embodiments of this invention, in which an angle of a tiltable mirror in a sample illumination beam path is adjusted.
Figure 10B:
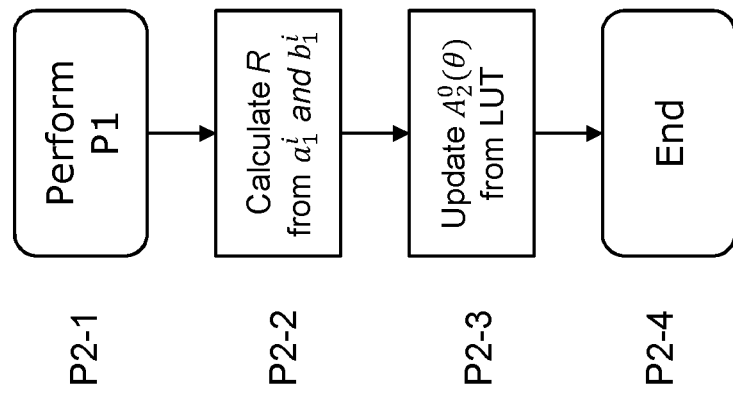
FIGS. 10a and 10b are flowchart diagrams illustrating steps of a feedback loop control process (P2) for sample based automated phase correction of a microscope according to embodiments of this invention.
Figure 10A:
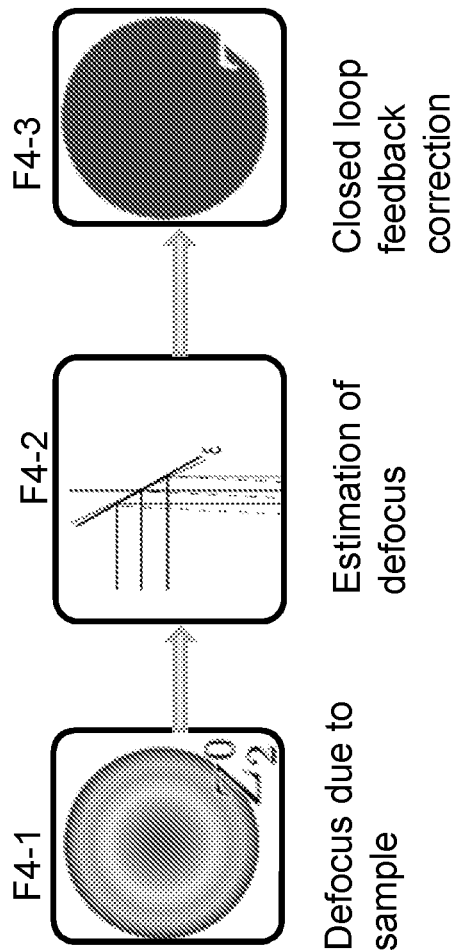
Figure 11:
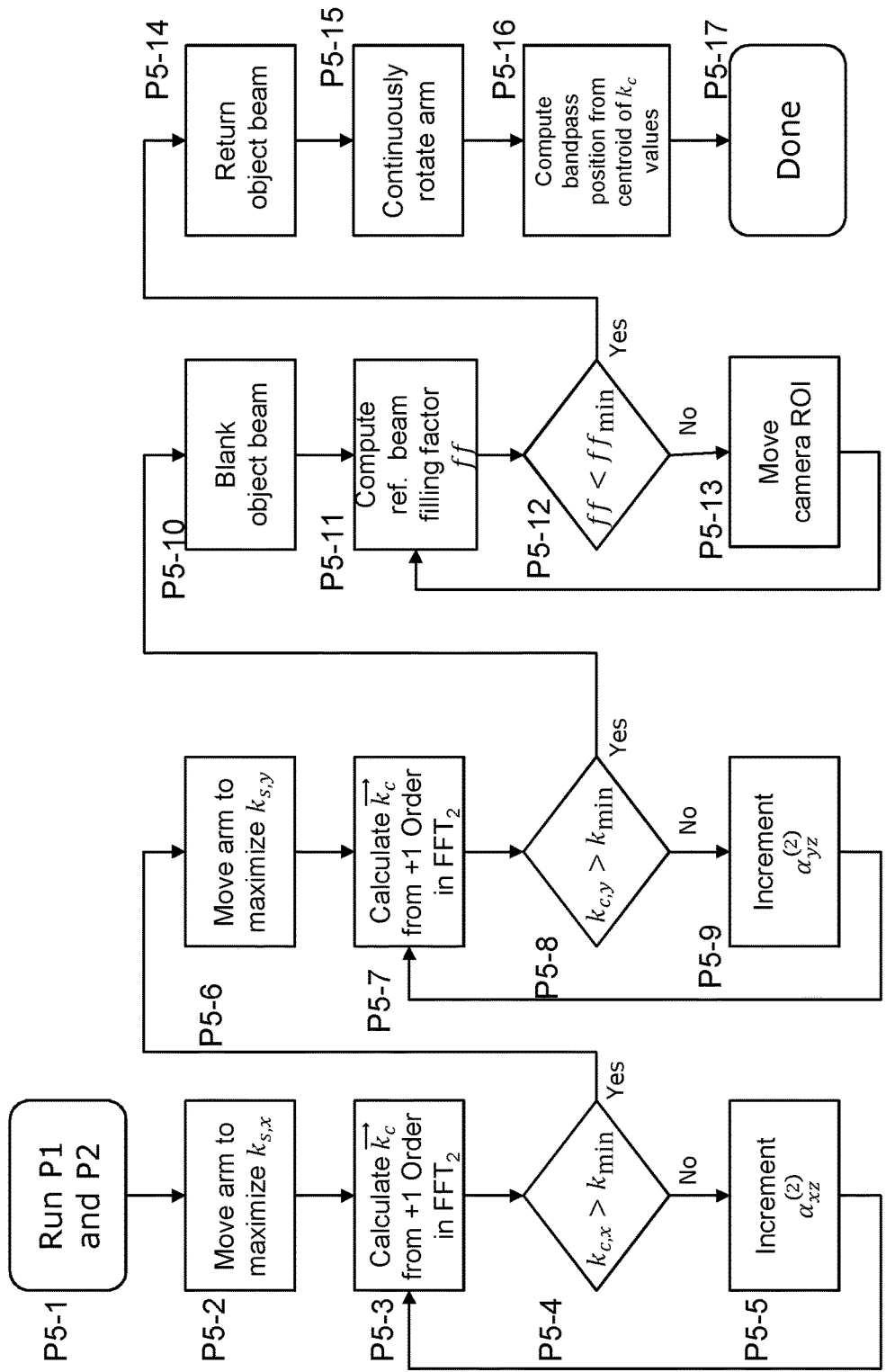
FIG. 11 is a flowchart diagram illustrating steps of a calibration process (P5) of a microscope according to embodiments of this invention, in which an angle of a tiltable mirror in a reference and sample illumination beam path is adjusted.

To circumvent these difficulties, in an embodiment illustrated in FIG. 8, a two-step process as described hereafter may be implemented. Under the assumption that the dominant Fourier coefficients are the DC and fundamental frequencies, a first step acquires approximations of these coefficients so that the feedback loop must only be able to react to the higher harmonic terms which exhibit much lower amplitudes. First, positions of the tiltable mirror centering the spot in the camera's 8 field of view are found for two orthogonal static positions θ1,θ2 of the rotating beam mechanism ("angles 1 and 2" in the flowchart of FIG. 9, θ1 and θ2 below)—see steps P1-1 to P1-5 and P1-6 to P1-10. This is done by moving the tiltable mirror (e.g. MEMS mirror) in a search pattern until the spot enters the camera's field of view (steps P1-2, P1-3 and P1-8, P1-9). A PID control is then used to center the spot in the image (step P1-4, P1-9). The thus obtained mirror angular positions may be saved (step P1-5, P1-9) and allow the calculation (step P1-11) of the DC and fundamental Fourier coefficients corresponding to the angular offset and circle radius and phase. This can be done by solving the 6 equations:

$$b_0^x + a_1^x \sin\theta_1 + b_1^x \cos\theta_1 = x_{m1}$$

$$b_0^y + a_1^y \sin\theta_1 + b_1^y \cos\theta_1 = y_{m1}$$

$$b_0^x + a_1^x \sin\theta_2 + b_1^x \cos\theta_2 = x_{m2}$$

$$b_0^y + a_1^y \sin\theta_2 + b_1^y \cos\theta_2 = x_{m2}$$

$$a_1^x = F b_1^y$$

$$b_1^x = -F a_1^y$$

for the 6 Fourier coefficients a and b. Here, the subscript m indicates the x and y values obtained from measurements for angles 1 and 2, and F is the sensitivity ratio between the x and y directions of the tiltable mirror.

Next, the rotating beam system (for instance referring to the arm of the mechanically rotated system illustrated in the embodiment of FIGS. 1a, 1b) is rotated continuously (step P1-12) and the previously determined offset and circular motion are dynamically applied to the tiltable mirror TM1 (step P1-13). The dominant portion of the incident light spot's motion is thus subtracted and the residual motion is slow enough to be followed by the feedback loop, i.e. PID control (step P1-14). The position may be saved (P1-15) and after a complete revolution the Fourier transform (P1-17) of the feedback loop's output signal can then be added (P1-18) to the previously obtained Fourier coefficients (i.e. DC and fundamental frequency values) resulting in the complete correction spectrum.

If necessary (P1-16), a second iteration can be performed, now applying all the obtained Fourier coefficients to the mirror TM1 (e.g. a MEMS mirror) during rotation and using the feedback loop of the electronic control system to again minimize the residual spot motion. This can be useful when changing rotation frequencies as the MEMS mirror's response is, in general, frequency-dependent and thus the coefficients may change with the rotating beam's angular speed.

Sample Phase Correction Procedure P2—Example of Feedback Loop Control of Tiltable Mirror for Sample Based & Automated Phase Correction This routine has the goal of finding a parameter for accessing a range of the lookup table (LUT) used to numerically correct a systematic error in the phase flatness of an acquired image. The laser sample illumination beam impinging on the sample may be slightly uncollimated. This may be due to a misalignment of the collimation optics but also due to the diffraction-limited divergence of a Gaussian beam. When changing the optical thickness of the sample through which this beam must travel, the curvature of the phase front in the microscope objective's field of view (FOV) is modified in the form of a defocus (Zernicke $Z_2^0$) aberration. It has been observed that this defocus aberration depends on the azimuthal angle θ of the rotating illumination arm and the optical thickness nh of the sample, where n is the sample medium's refractive index. As the aberration does not change from sample to sample, a pre-determined LUT can be used to numerically correct the defocus effect, given θ and nh.

The optical thickness nh of the sample can be deduced from the results of calibration procedure P1. It may be noted that procedure P1 may be performed to compensate for a sample-thickness h1, h2 (see FIG. 16d) dependent walk-off of the sample illumination beam from the microscope objective's field of view (FOV).

As the tilting mirror TM1 positioned upstream of the rotating beam system is mounted statically, the rotation of the rotating beam system 38 causes the correction by the tiltable mirror TM1 to be dynamic. However, the dominant component is a circular correction, corresponding to a constant angular deflection in cylindrical coordinates (α' above). In procedure P1, the circular motion is described by the first order Fourier coefficients $a_1^i$ and $b_1^i$, the motion's radius given by $$R = \sqrt{(a_1^x)^2 + (b_1^x)^2} = F\sqrt{(a_1^y)^2 + (b_1^y)^2}.$$

The radius R is directly proportional to the shift in the angle α'. Due to Snell's law, there is no linear relation between nh and α', thus between nh and R. However, if a look up table (LUT) is used to characterize the nh-dependence of correction parameter $A_2^0$, any nonlinearity can be compensated by the LUT itself, as long as the nonlinearity was taken into account during creation of the LUT. In this case, the LUT parameter can be directly defined by the radius R.

The procedure steps can be listed as follow:

P2-1 After having performed calibration procedure P1, compute R from the first order Fourier coefficients $a_1^i$ and $b_1^i$ as described above.

P2-2 Update the corresponding LUT index from which to extract the correction coefficients $A_2^0(\theta)$.

As the defocus correction $A_2^0$ is applied for each acquired hologram separately, the corresponding LUT parameter θ is determined at runtime, e.g. exploiting an angular position sensor or using the hologram's carrier frequency.

In a variant, the above procedure is performed using lower harmonics (i.e. the DC Fourier components $b_0^i$) and higher harmonics for the walk-off compensation, allowing detection of a nonuniform sample thickness (e.g. a tilted dish containing liquid or a warped surface). In this case, the rotation symmetry above is broken and the LUT parameter R, itself, depends on the rotation angle: $A_2^0 = A_2^0(R(\theta), \theta)$.

In a variant, the optical thickness nh is determined from the optical path length compensation performed in P3/P4. There, the optical path difference induced by the sample thickness nh is compensated by a moving element. The position of the moving element can conversely be used to deduce nh. Similarly to above, nh is nonlinearly dependent on the moving element position, but this nonlinearity can be compensated by an appropriately calibrated LUT. Vice versa, the estimation of nh deduced by procedure P2 may be used to position the moving element in P3/P4.

Reference Beam Correction Procedure P5—Example

This routine has the goal of finding an optimal setting for tilting mirror TM2 so that the observed holographic fringes have a frequency which optimizes the demodulated phase image's signal-to-noise ratio (SNR). The holographic fringes are created in the microscope by superimposing two light beams on the light sensing system 8 (e.g camera), namely the object beam and the reference beam. Assuming both beams are plane waves with wave vectors $\vec{k}_r$ and $\vec{k}_s$, the intensity on the camera can be written as:

$$I(x, y) = 2 + e^{i(\vec{k}_r - \vec{k}_s)\vec{r}} + e^{i(\vec{k}_s - \vec{k}_r)\vec{r}} \quad (1)$$

where $\vec{r} = (x, y, z_c)$ and $z_c$ is the z-position of the camera. While both beams exhibit a spherical curvature, the radii are the same in both cases and can be subtracted during superposition. The reference beam's direction can thus indeed be described by a single wave vector $\vec{k}_r$. Similarly, the object beam comprises a main component $\vec{k}_s$ modulated by the object through which it has passed. The object beam's carrier frequency follows the direction of the rotating incident illumination, its in-plane component describing a circle around the origin, as described by the dotted circle in FIG. 14*a*. The arrow denotes the in-plane wave vector of the reference beam. The Fourier transform of the intensity pattern described in Eq. (1) is shown by the −1 order and +1 order circles: the constant term is displayed by the black dot near the origin and the second and third summands are the circles, named "+1 Order" and "−1 Order", respectively. In order to accurately process the holograms, the spectrum of the superimposed waves' intensity pattern (i.e. −1 order and +1 order circles above, called the carrier frequency $\vec{k}_c$) must be spatially separated from the constant term described by the black centre dot. In addition, the entire circle should be in a single quadrant of the spectrum, speeding up processing as only a single quadrant must be regarded.

Introducing a tilt in the reference wave corresponds to multiplying its expression with a linear phase function, which direction is defined by the vector kr. The tilted reference wave hence becomes rt=re−i(kr·x), where x=(ex,ey,ez) is the unitary vector of the Cartesian coordinate system:

$$I = |o|^2 + |r|^2 + o^* r e^{-i(k_r \cdot x)} + o r^* e^{i(k_r \cdot x)},$$

One can identify that the interference terms are multiplied with various phase factors, which correspond in the SFD to different modulations. If one considers the modulation frequency along an axis ωx parallel to the modulation direction, the inclination angle θ will induce a modulation frequency corresponding to $$|\omega_\theta| = \frac{\sin\gamma}{\lambda} = \frac{\sin 2\alpha^{(2)}_{xyz}}{\lambda}$$

On the other hand, the detector has a sampling capacity in the x direction corresponding to a frequency of ω=1/Δx, where Δx is the pixel size of the camera. By considering the Nyquist theorem, the maximum angle which can be resolved by the detector is thus $$|\omega_{0,x}| = \frac{\sin 2\alpha^{(2)}_{xyz} \cos\phi}{\lambda} \leq \frac{1}{2\Delta X}$$

$$\alpha^{(2)}_{xz} \leq 2\sin^{-1}\left(\frac{\lambda}{\Delta X \sqrt{2}}\right)/4 \Rightarrow \sin 2\alpha^{(2)}_{xyz} \leq \frac{\lambda}{\sqrt{2}\,\Delta X}$$

According to this equation, for the main laser line of λ=520 nm and a standard pixel size of a CCD camera (Δx=5 μm), the maximal usable angle is Y≤4o and α(2)≤2o. In order to enable measurement of diffracted wave vectors, one can consider in first approximation limiting the angle to one half of this value, putting the carrier frequency at the center of the quadrant, thus yielding α(2)≤1°. Assuming a maximal band pass shift of band pass/8, hence 512px/8=64px, the maximum shift results in Δα(2)≤0.25°.

Given a maximum distance of 300 mm from the tiltable mirror TM2 to the light detector 8, a maximum shift results in Δα(2)≤0.25° results in a lateral real space displacement of) tan(0.25°)*300 mm=1.3 mm. For a typical sensor size 1024*0.005 mm=5.12 mm, a beam size of 6.4 mm should be hence sufficient to adapt the carrier frequency only α(2) without losing intensity in real space diameter_ref=FOV+ maximum displacement.

The position of the intensity pattern's spectrum is dependent on both the object 7*b* and the reference 7*a* beam's direction. As the geometry of the microscope objective 37 in relation to the camera 8 is fixed, the object beam's direction can not easily be adjusted. The reference beam's direction, however, can be adjusted using a tiltable mirror, e.g. TM 2. A procedure for finding an optimal position for tiltable mirror TM2 may be as follows:

P5-1 Calibration procedures P1 and P2 are first run through to ensure that there are fringes observable on the light detector 8.

P5-2 Rotate the object beam 7*b* by means of the rotating beam system 36 (for instance rotating the support arm 40 in the embodiment illustrated in FIG. 1*b*) to maximize the $k_x$-component of the object beam's wave vector.

P5-3 Compute the 2D FFT of the intensity pattern on the light detector (camera) 8 and calculate the carrier frequency $\vec{k}_c$ from the +1 Order.

P5-4 Compare with a pre-defined minimum value $k_{min}$. If $k_{c,x} > k_{min}$, proceed to step P5-6.

P5-5 Increment the tilting mirror TM2 so that the reference beam 7*a* falls more steeply on the x-axis of the camera 8. Return to step P5-3.

P5-6 Rotate the object beam 7*b* by means of the rotating beam system 36 (for instance rotating the support arm 40 in the embodiment illustrated in FIG. 1*b*) to maximize the $k_y$ component of the object beam's wave vector.

P5-7 Compute the 2D FFT of the intensity pattern on the camera and calculate the carrier frequency $\vec{k}_c$ from the +1 Order.

P5-8 Compare $k_{c,y}$ with a pre-defined minimum value $k_{min}$. If $k_{c,y} > k_{min}$, proceed to step P5-10.

P5-9 Increment the tilting mirror TM2 so that the reference beam falls more steeply on the y-axis of the camera. Return to step P5-7

P5-10 Blank the object beam 7*b* by tilting the mirror TM1 in the object beam path (positioned upstream of the sample 1), completely to one side so that only the reference beam 7*a* falls on the light detector 8.

P5-11 Compute the filling factor ff of the reference beam by calculating the portion of pixels in the camera region of interest (ROI) that are illuminated.

P5-12 Compare ff with a predefined value $ff_{min}$. If $ff \geq ff_{min}$, proceed to step P5-14

P5-13 Move the ROI away from the mean position of the non-illuminated pixels. Return to step P5-11.

P5-14 Return the object beam tiltable mirror TM1 to its default position to see the object beam on the light detector.

P5-15 Continuously rotate the object beam (e.g. rotating the support arm 40).

P5-16 Acquire multiple holograms and compute the centroid of their carrier frequencies as the center of the bandpass filter used for demodulation.

P5-17 End of Procedure.

Figure 12:
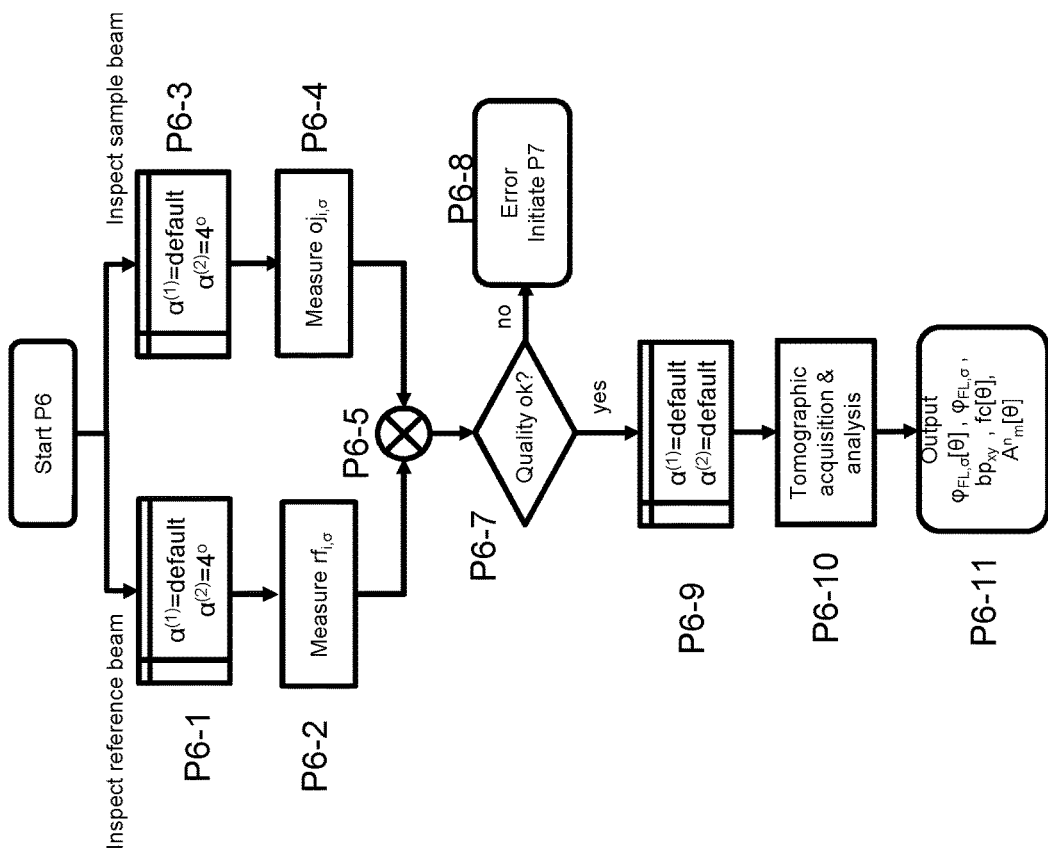
FIG. 12 is a flowchart diagram illustrating steps of a quality assessment process (P6) of a microscope according to embodiments of this invention, in which an angle of a tiltable mirror in a reference beam path is adjusted.

Quality Assessment Procedure P6—Example Referring to FIG. 12

This routine has the goal of assessing the quality of a measurement by extracting some features of the optical beams, when no sample is present in the field of view: intensity mean value waviness and roughness. The goal of this procedure is to furnish i) information on beam intensity distributions (that can be used to diagnose a problem) and ii) a LUT for the A_n^m, which remain to be determined after procedure P2, where $n \leq 2$ and $m \leq 1$. If a sample 1 is inserted into the object beam 7b path, a lightened procedure must be applied to make sure that the sample is basically in the ad-hoc shape to allow proper 3D measurements.

Depending on the type of observed samples, the nature of the mounting medium and the state of cleanness of the optical surfaces, the intensity distribution can be more or less altered. Moreover, even when beam uniformity fulfills some quality requirements, the phase of each hologram may not be perfectly flat due to remaining slight misalignments in the optical paths. To allow best quality tomographic measurement, and once the first orders aberration have been compensated, namely piston, tilt and defocus, the higher order aberrations may be quantified and numerically compensated, as described in procedures P3 or P4.

At this stage of the calibration of the device, the procedures P1, P2, P3/4 and P5 have been conducted. We may now ensure that the full field of view is empty of defects which may come out as non-uniformity in the intensity distribution of the object and/or reference beam. Alternatively, as described in FIG. 18, P6 may be conducted after applying P1, P3/4, and P5, on a empty FOV hence yielding for a LUT of parameters A_n^m which are solely due to the microscope's optical properties. Following procedure P2 serves to update A_2^0 which is due to the sample induced optical properties.

An approach is thus here to first use the tilting mirror TM2 in the reference beam 7a optical path to mask the reference beam with respect to the light detector 8. The object beam 7b can then be characterized. The same procedure may be carried out for the reference beam when masking the object beam by tilting mirror TM1. If an error is detected at this point, the procedure P7 may be launched, otherwise, a tomographic acquisition may be carried out, meaning a sequence of holograms is acquired and analyzed.

Once the beam uniformity fulfills some predefined quality criteria, a sequence of holograms, is recorded and analyzed, as previously described. From each hologram retrieved during a revolution of the rotating object beam relative to the sample 1, the phase $\varphi[\theta]$ of the beam signal retrieved by the light detector is calculated and characterized in terms again of flatness and roughness. For each rotating beam system angle, a least-squares fit to the Zernicke polynomials R_n^m may be calculated to produce a lookup table (LUT) of the values of A_nn^m parameters. From this LUT, a flat phase can be retrieved for every orientation of the rotating beam system and a tomographic reconstruction can be achieved (still of an empty field of view). In addition, this method is prone to statistical characterization from this 3D measurement, which can be compared to quality criteria in terms again of flatness and roughness.

Error Analysis Procedure P7—Example Referring to FIG. 13

When an error occurs, this procedure is launched to solve the problem or diagnose it as much as possible to send useful information to a computer network (herein named the Cloud) in the form of a log file. If after several testing routines, the device still does not work properly, maintenance might be required.

We only consider here failures in the above described routines from P1 to P6. This error routine P7 describes how the system is able to self-diagnose a problem and solve it or gives basic and precise instructions to the user to do so. Two types of problems are considered: a problem linked to i) the sample, either it be the nature of the sample (absorption, thickness), or the nature of the medium in which the sample is immersed (diffusing or exhibiting floating debris) or to ii) the optics, for instance due to dust or a misalignment.

The approach is the following when an error is detected which prevents from carrying out proper tomographic measurement, or simply from completing one of the procedures P1 to P6. In a first step, the device connects to the cloud in order to upload a log files containing meta-data. A second step is to carry out a blind global search in 2D of the object beam 7b by pivoting of the tiltable mirror TM1. This search is said to be blind as no specific constraints are given to restrict the search pattern within the range of possible tilt angle of TM1. This procedure occurs either during the microscope start-up, for instance without sample 1, or after a sample has been inserted in the sample observation zone 17.

Later on, a constrained global search may be made on the reference beam tiltable mirrors TM2 to TM4, whereas constraint is given by parallel orientation of TM3 and TM4 as function of movable element or angle ranges of TM2 This step aims at identifying if the problem, not solved by the previous steps, could actually come from the reference optical path. The search is constrained here as the motions of the mirrors are, by design, connected by linear laws. It also allows reducing the complexity of the search and thus speeding it up.

After having performed those two global searches, the procedure P6 can be done to assess the quality of the measurement. From there, the problem is either solved or further analysis is required, which is then performed for different orientation of the rotating light guiding system. An individual and computation-intensive analysis may be applied to the sample illumination dependent series of holograms. It aims at defining whether the problem is orientation dependent or not.

It can then be deduced if the problem comes from the optics or the sample, and oriented instructions could be given to the user. If the quality is not satisfying yet, then the device can be remotely accessed for more advanced analysis. If the problem remains after this procedure, the device requires special care.

Figure 18:
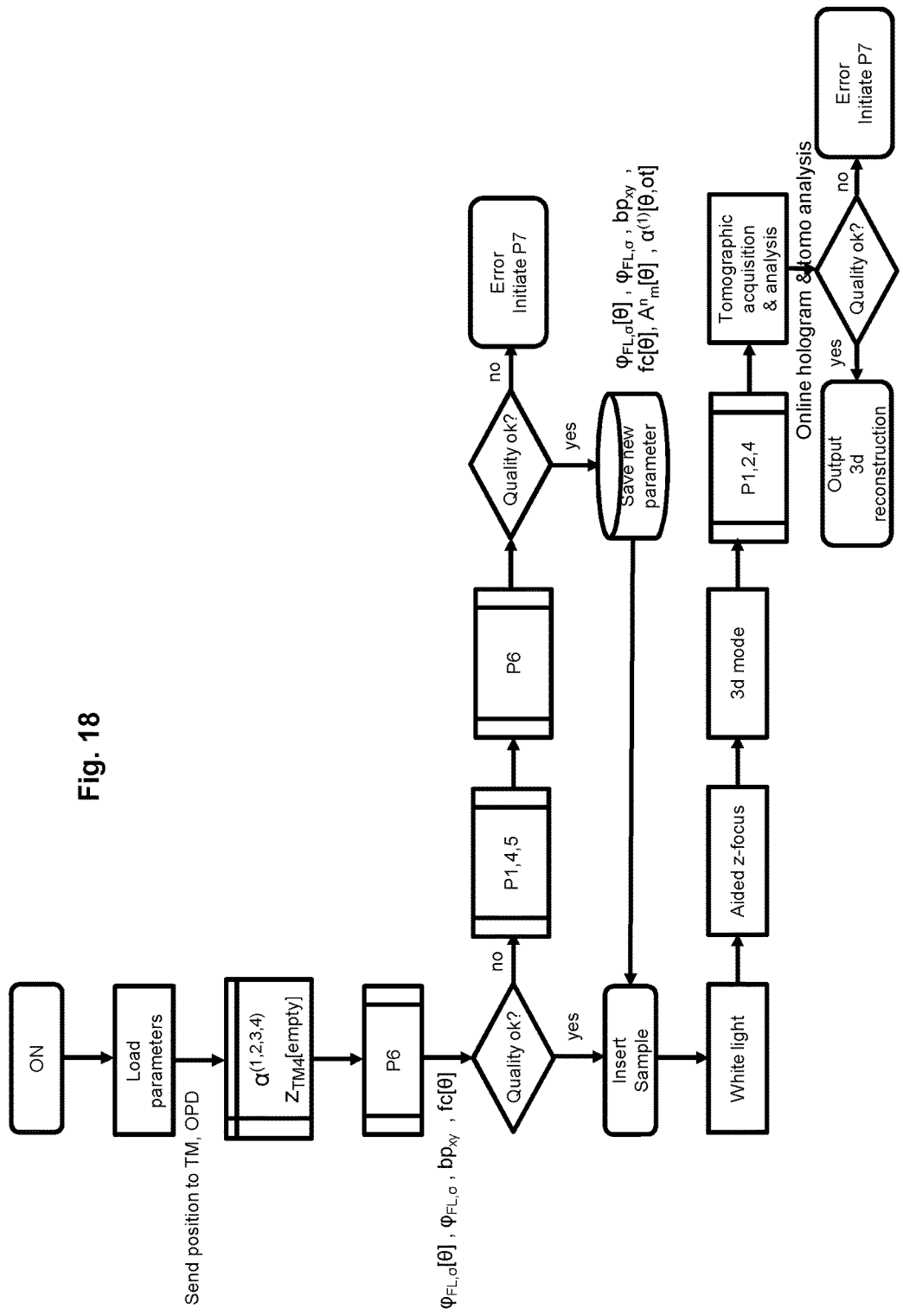
FIG. 18 is a flowchart diagram illustrating overall the implementation of the various procedures P1 to P7 in the operation of a microscope according to an embodiment of the invention.

FIG. 18 illustrates an example of the overall implementation of the various procedures P1 to P7 in the operation of a microscope according to an embodiment of the invention.

An amplitude and phase analysis of individual holograms captured by the light sensing system in each of the procedures P1 to P7 described above is explained hereafter. The different levels of feedback can be viewed in an onion peel model, the outer surface of which describes the most accessible level while the innermost core is the least accessible. Access to each level first requires a successful alignment of all outer feedback levels. In particular, the different levels of feedback control can be described using an onion peel model with the subsequent levels intensity, coherence, fringe frequency and phase as shown in FIG. 14b. Each feedback level can be accessed in one or more of the presented calibration procedures and represents not only a monitor for the calibration quality but also a parameter which must be optimized before proceeding inwards: all outer layers must be successfully calibrated before the next layer can be assessed. The innermost layer, the imaged phase, is finally the value used for imaging biological samples in the microscope. The first layer, the intensity, is the least complicated parameter to adjust as it requires no alignment of the other parameters. The intensity of the object and reference beams are optimized if the beams pass neatly through the clear apertures of all optical elements in the beam path. Initially, a proper alignment must be found only once, but the intensity must be adjusted each time the configuration is modified during the alignment of the other feedback parameters. One special case of intensity alignment is the calibration procedure P1, as it entails the determination of a dynamic correction that ensures that the intensity maximum of the object beam remains centered on the microscope objective's FOV during rotation of the sample illumination beam. The intensity layer can also provide information on the sample and the configuration of the system. For example, the coefficients obtained in procedure P1 can give an estimate of the sample's optical thickness, as is used in P2. Also, in an embodiment where mirror TM4 is both tiltable and translatable, the angle of the tiltable mirror TM3 in the reference beam path at which light passes through the clear aperture of the tiltable mirror TM4 can give an approximation of the position of translatable mirror TM4.

The second layer, the coherence, is optimized if the optical path lengths of object and reference beams are shorter than the light source's coherence length. This is equivalent to a fixed phase relation between the object and reference beams and is required for interference fringes to be observed. It is obvious that in order to obtain fringes, the intensity of both object and reference beams must be properly optimized, i.e. the outer layer must be successfully aligned. Conversely, after optimizing the optical path lengths, the intensity alignment should be verified. Besides providing a prerequisite for interference, the configuration for optimal coherence is also a measure for the optical thickness of a sample in the object beam path.

The third layer, the fringe frequency, is defined by the relative angles of the reference and object beams incident on the light sensing system. In contrast to the intensity, this layer is influenced by the angle at which the optical elements in the beam path are passed through. This layer is optimized if the fringe frequency is large enough so that the modulated image information in the pass band around the observed hologram order does not overlap the 0 order region. The fringe frequency is further optimized if the fringe direction is such that the carrier frequency peak in the corresponding spectrum is in the same quadrant for all rotational positions of the rotating sample illumination beam relative to the sample, thus speeding up processing. The proper alignment of intensity and possibly also coherence must be verified after modifying this layer.

The fringe frequency, i.e. the position of the carrier peak in the hologram's Fourier transform, can be used to extract useful information at run-time, namely during acquisition. For example, the peak's maximum defines the frequency that must be used for demodulation. The peak's position relative to the centroid of its rotation upon turning the sample illumination beam relative to the sample can be used to calculate the angular position of the rotating beam system relative to the sample, to be used for look up table (LUT) based corrections of the phase.

The innermost layer, the phase of the demodulated image, may be used to reconstruct an image of the sample 1. This value is obtained by acquiring a hologram, applying a filter to the previously determined pass band in its spectrum, and successfully demodulating the carrier frequency. It can be seen that all outer layers must be optimized before assessing the phase. Given an empty sample containing the medium but not the biological object, this parameter is optimized if the phase of the resulting image is optimally flat. This phase flatness can be degraded by a suboptimally corrected microscope objective, but also by incorrectly placed optical elements in the microscope, such as:

I. Passing a non-collimated beam through a flat window.
II. Passing a beam through a lens obliquely, i.e. not parallel to the lens's optical axis.

The above aberrations, particularly no. II., can be minimized using optimization routines to control the beam position and incident angles onto the optical elements. Residual phase errors can be corrected numerically if a sample-free reference is provided.

Referring to FIG. 15, phase correction for the auto calibration steps is explained hereafter. An object scanning feedback for optical thickness estimation is performed through the control of tiltable mirrors. It allows sample based and automated phase correction, meaning user independent correction without background identification, and which is capable of dealing with high cell confluency.

The optical aberrations introduced during the imaging process can be described regarding the phase transfer from objet to image. It is assumed that the phase of the object $\varphi_o(\vec{r})$ is modified by a phase offset $\varphi_s(\vec{r})$ of the optical system. The light fields can thus be written as $$E_i(\vec{r})e^{i\varphi_i(\vec{r})}=E_o(\vec{r})e^{i\varphi_o(\vec{r})}e^{i\varphi_s(\vec{r})}=E_o(\vec{r})e^{i(\varphi_o(\vec{r})+\varphi_s(\vec{r}))}$$

Here, the index i denotes the image, o denotes the object and s denotes the optical system. If the aberrations in the form of $\varphi_s(\vec{r})$ are known, a correction phase factor $\varphi_c(\vec{r})=-\varphi_s(\vec{r})$ can be derived with which the undistorted object field can be reconstructed:

$$E_o(\vec{r})e^{i\varphi_o(\vec{r})}=E_i(\vec{r})e^{i\varphi_i(\vec{r})}e^{i\varphi_c(\vec{r})}$$

Figure 15A:
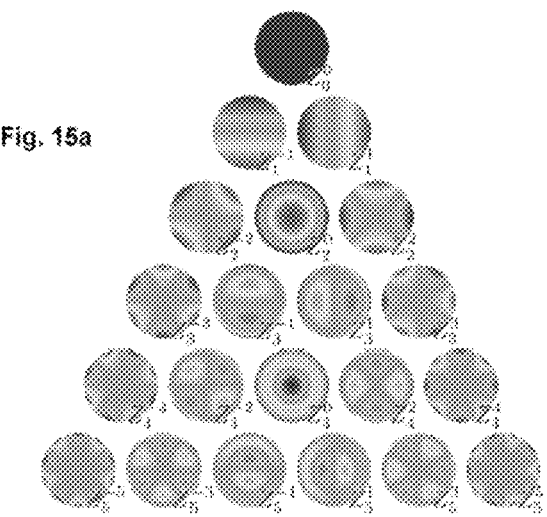
FIG. 15a is an illustration of diagrams of aberrations of different orders captured by the light sensing system of a microscope according to embodiments of the invention, for use in amplitude and phase analysis of the beam received by the light sensing system.

The phase offset $\varphi_s(\vec{r})$ can be expanded in a series of polynomials called Zernike polynomials $Z_n^m$, m=−n . . . n. These polynomials are depicted in FIG. 15a. Accordingly, the correction factor can be reduced to a set of parameters $A_n^m$ with $\varphi_c(\vec{r})=-\Sigma_n^m A_n^m Z_n^m(\vec{r})$. To numerically correct for aberrations after a measurement, the parameters $A_n^m$ must be determined.

For an empty sample, namely a medium (e.g. a liquid) without biological sample immersed therein, $\varphi_i(\vec{r})$ is constant and so the phase measured e.g. by a holographic microscope describes the pure aberrations. An analysis of the present aberrations indicates their respective origins. $Z_1$ aberrations, i.e. tilt, depend only on the orientations θ and α of the illumination and their magnitude can directly be determined from the carrier frequency in each hologram. Most higher order aberrations (m≥2) are characteristic to the imaging system and independent of the sample, hence these aberrations can be characterized without sample, their corresponding correction parameters $A_n^m$ stored in a reference table. A special case is the defocus aberration, $Z_2^0$, which is composed of a system-defined component and a component depending on the sample thickness nh and illumination direction. The corresponding correction parameters $A_2^0$ must thus be stored in a reference table with additional parameters for nh and θ.

Tilt (Z1 aberrations, A_1^(±1) factors) for each acquired hologram can be determined directly from the hologram's Fourier transform (special frequency domain, SFD) or through a least-squares fit in real space to the phase of a hologram frequency filtered to contain only one non-zero order (or by a combination of the two approaches). The correction factors are directly proportional to the position of the hologram's carrier peak, respectively the slope of the plane fit by least-squares.

The carrier wave frequency (respectively peak position in the SFD) can be used to determine the angular position θ of the rotating beam mechanism relative to the sample. Here, the position of the carrier peak must be determined with respect to the centroid of the circle described by the carrier peaks during a complete rotation of the rotating beam mechanism. This center can easily be found given three carrier peaks: the centroid is the intersection of the perpendicular bisectors of the line segments connecting the three peak positions. Given the rotating beam mechanism position θ, the remaining correction factors A_n^m can be obtained by inserting θ (and the sample thickness) into a lookup table. This lookup table is previously populated from calibration measurements on transparent, homogeneous samples such as in procedure P6. For various sample medium thicknesses nh and rotating beam mechanism angles θ, the uncorrected phase is measured and a least-squares fit to the Zernicke polynomials R_n^m yields the lookup table values.

Figure 15C:
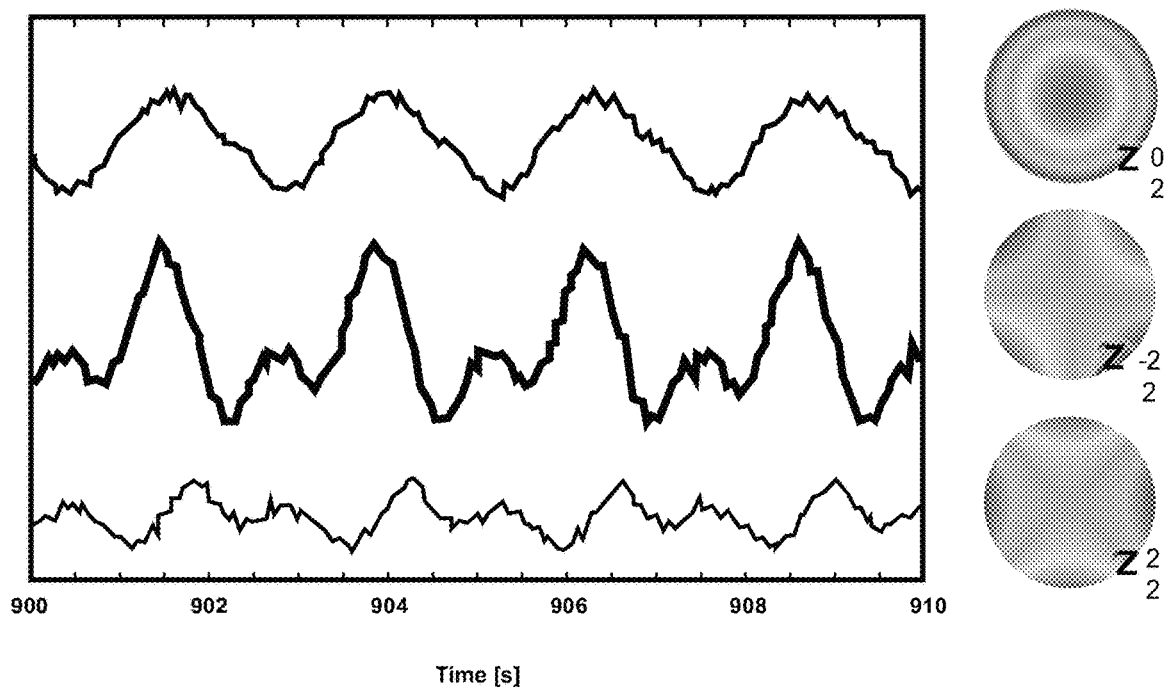
FIGS. 15b and 15c are graphical representations of a signal generated by aberrations of different orders captured by the light sensing system of a microscope according to embodiments of the invention.
Figure 15B:
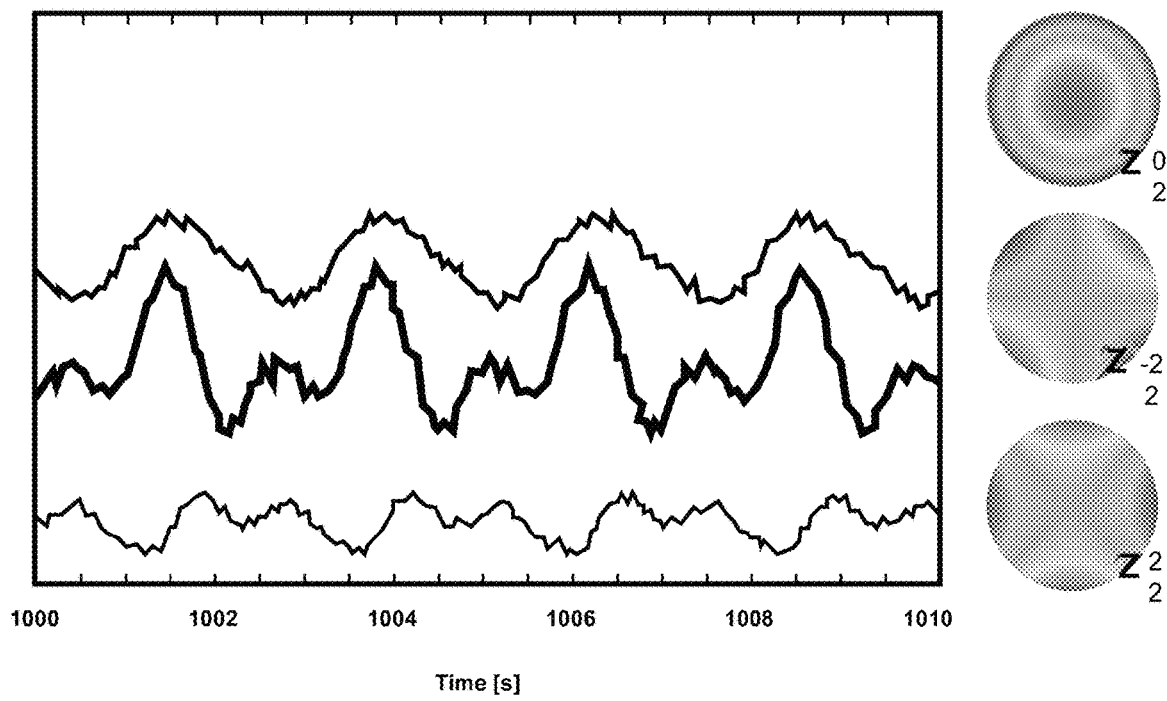

Referring to FIGS. 15b and 15c, typical measurements, represented by higher order development as function of time (during rotation), of astigmatisms and defocus in different sample conditions is illustrated. In FIG. 15b, the sample is provided by a coverslip for which defocus is only a function of rotation, the magnitude of the defocus' offset is determined by the optical thickness, and astigmatism is constant in time and dependent on rotation. In FIG. 15c, the sample is in a Petri dish whereby defocus may be a function of rotation and evaporation (changing in time), the magnitude of the defocus' offset is determined by the sample's optical thickness and a possible meniscus, and astigmatism is constant in time and dependent on rotation.

These measurements tell us that the mean magnitude of defocus varies with the sample's optical thickness. Therefore, the goal of a scan by varying the angle of a tiltable mirror in the sample illumination path is to determine the sample's optical thickness and by these means the magnitude of defocus. In case of an aqueous solution, a meniscus may introduce additional defocus. For best defocus estimation, a measurement of eg theta dependence (during calibration) of defocus could serve as meniscus estimation (amongst others).

Figure 16A:
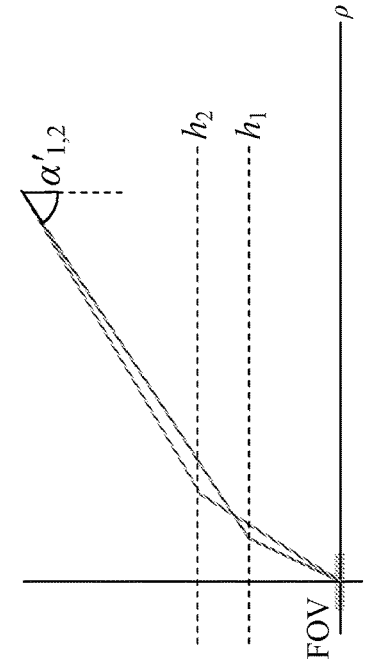
FIG. 16a is an illustration of geometrical angles and lengths of a sample illumination beam at an interface between matter of two different refractive indices n1, n2, for illustration of a sample immersed in a liquid of height h.
Figure 16B:
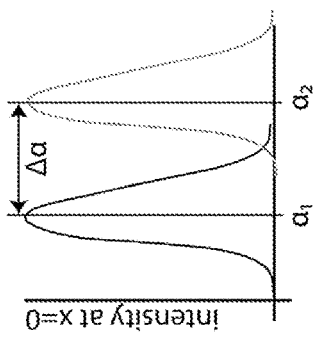
FIG. 16b is an illustration of the relationship between intensity of the measured beam signal and a defocus angle ($\Delta\alpha$)
Figure 16C:
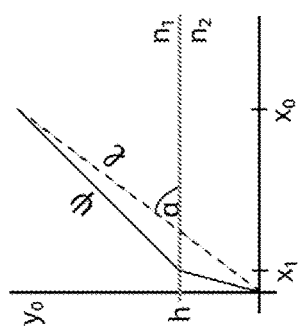
FIG. 16c is an illustration of the relationship between the defocus angle ($\Delta\alpha$) of the sample illumination beam and the height of the sample liquid to determine the phase correction ($\varphi$)
Figure 16D:
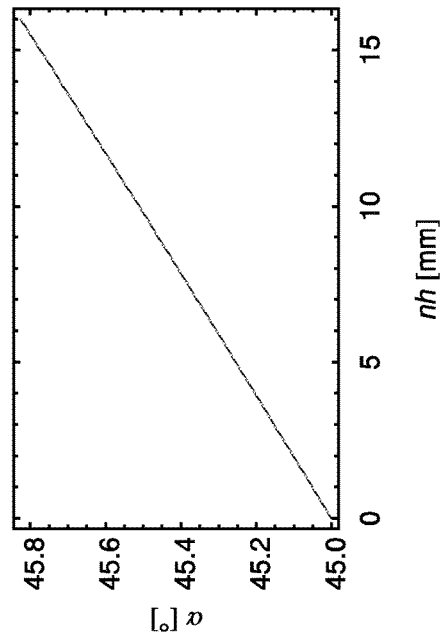
FIG. 16d is an illustration regarding a sample-thickness h1, h2 dependent walk-off of the sample illumination beam from the microscope objective's field of view (FOV)

Referring to FIGS. 16a-16c, an estimation of the prefactor mentioned above is explained. During a scan in which the angle of the tiltable mirror is varied, measurement of the light beam signal captured by the light sensor (e.g. camera) of the light sensing system provides the following information: the intensity in the center of the field of view, i.e. at (x=0), will show a maximum if the incident light's angle α is such that the light beam falls directly into the field of view. This is the case displayed in FIG. 16a for the solid line. For a varying optical thickness thickness nh of the sample, this maximum will shift to a different α, as displayed in FIG. 16b. The relation between the angle α and the optical thickness can be given using Fermat's principle and involves minimizing the optical path ψ for a given geometry:

$$\psi = n_2\sqrt{h^2+x_1^2}+n_1\sqrt{(y_0-h)^2+(x_0-x_1)^2}.$$

Here, $(x_0,y_0)$ is the position of the beam reflected off of the tiltable mirror and $(x_1, y_1)$ is the position of the beam entering the sample medium. A nonlinear relation between α and the optical thickness nh can thus be derived, but for optical thicknesses small compared to the distance to the mirror, the response is nearly linear, as shown in FIG. 16c for typical values in the microscope.

$$\psi = \sqrt{n2^2(h^2+x1^2)} + \sqrt{n1^2((x0-x1)^2+(-h+y0)^2)}$$

$$d\psi = \frac{n2^2 \times 1}{\sqrt{n2^2(h^2+x1^2)}} + \frac{n1^2(-x0+x1)}{\sqrt{n1^2((x0-x1)^2+(h-y0)^2)}} = 0|$$

Figure 17A:
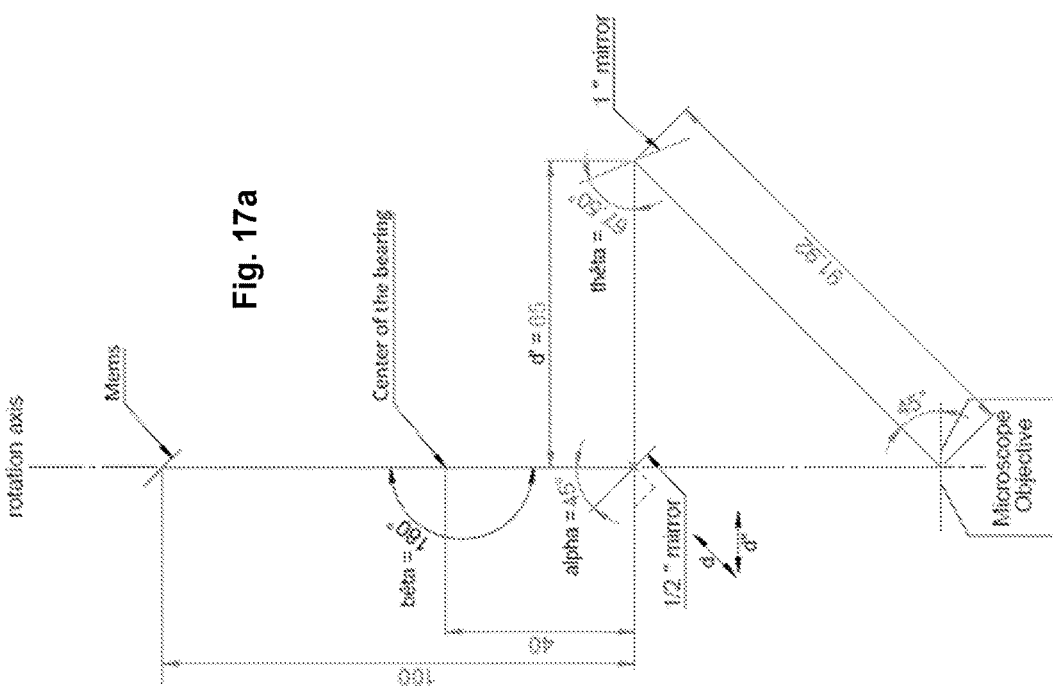

Example of Reduction of Tolerances on Mechanics and Compensation of Heat Diffusion Through the Use of Tiltable Mirrors:

Referring to FIG. 17a, an illustration of the sample illumination beam rotating head architecture is represented to study influences of mechanical tolerances discussed below. Changing parameters include
  alpha: angle of the central mirror 54 with respect to the optical axis A.
  beta: angle of the rotating beam system 28 with respect to the structure.
  theta: angle of peripheral mirror 56 with respect to the optical axis in neutral position.
  d: position of central mirror 54 in its normal direction.
  d': distance between the two mirrors 54, 56.
  d": horizontal position of the arm compared with the hollow shaft 58.

A chosen criterion is to be within a certain tolerance of the MEMS mirror 26b compensation angle, which may be for instance 0.1°, corresponding to a static error of its normal direction about its mechanical pivot axis.

Different combinations of errors have been studied and results are shown in the table of FIG. 17b. Tolerances that are aimed for may be for instance:
  d/d' and d": 0.1 mm (not very critical)
  alpha/beta/theta: 0.025° corresponding to 0.0055 mm for the geometrical tolerances.

As previously described, the tiltable transmissive or reflective elements of the OPD system may also be controlled by means of a feedback loop based at least partially on the light beam signal captured by the light sensing system to adjust and correct the path of the reference beam.

More generally, an important aspect of the invention is the use of feedback from the beam signal captured by the light sensing system to automatically control, by means of the electronic control system, the angle of the one or more tilt adjustable mirrors by the control system in order to correct for unwanted deviations of the sample illumination beam or the reference beam, or both the sample illumination and reference beams, or to create wanted deviations (e.g. to control the OPD). Deviations in the sample illumination path may be due to manufacturing tolerances, wear of components of the microscope over its lifetime use, thermal dilatation effects, or variations in the sample medium such as liquid height, meniscus curvature, non-horizontal liquid surface and other factors. Deviations of the reference beam may also be due to manufacturing tolerances, wear of components of the microscope over its lifetime use, and thermal dilatation effects, and also desired deviations to control the optical path difference. The control of these deviations in either the sample illumination beam or the reference beam by reading the beam signal captured by the light sensing system advantageously provides an automated manner to obtain high quality images in a simple, easy and cost effective manner with minimal setup.

Dynamic OPD Procedure P8—Example Referring to FIGS. 5f, 5g and 2c, 2d

Due to defects or simply imperfections in the mechanics, the length of the optical path (OPL) of the sample beam is likely to vary when the rotating scanning arm is completing a 360° rotation during the acquisition of the holograms. If those defects result in a OPL variation confined to a fraction of the coherence length of the laser, the procedure described in relation to FIGS. 4h-4i may be used to have optimum fringe contrast for any orientation of the scanning arm (see FIGS. 2c and 2d).

However, this defect may result in a variation of the optical path length beyond the coherence length reducing thus greatly or even cancelling the fringe contrast in certain orientations of the arm, making the phase calculation meaningless in those positions.

To compensate for this and find the minimal OPL as illustrated in FIG. 5g, the OPL is dynamically adjusted by the control system of the microscope to keep the OPD between the reference and sample beams far below the coherence length of the laser source and ensure an optimum fringe contrast along the rotational scanning process.

The method for defining the parameters that may be applied to the OPD system 32 synchronously with the rotating beam system 36 comprises the following steps:

a) place a sample on the sample holder,
b) position the rotating beam system in a first position,
c) position said at least one pivotally actionable direction change mirror (TM3, TM4) configured to direct the reference beam in a first position,
d) measure a position of the reference beam signal captured by the light sensing system while the sample beam is switched off,
e) switch on the sample beam and measure a fringe contrast of a signal captured by the light sensing system
f) change by an increment the position of said at least one pivotally actionable direction change mirror (TM3, TM4),
g) repeat steps d) to f) until the sum of increments corresponds to a pre-defined working range of the pivotally actionable direction change mirror (TM3, TM4),
h) compare the fringe contrast measurements obtained for each increment and store in look-up table (LUT) of a memory of the control system the position of the pivotally actionable direction change mirror (TM3, TM4) for the fringe contrast measurement with the highest value, in conjunction with the position of the rotating beam system;
j) rotate by a small increment the rotating beam system and repeat steps c) to h) until the rotating beam system has completed a 360° rotation.

A look-up table (LUT) may thus be created to provide the parameters that can be applied to dynamically control the OPD system 32 synchronously with the rotating beam system 36.

By way of example, this procedure is illustrated in the embodiment of FIG. 5f, which comprises the following steps:

Once a sample is placed on the XY stage (step P8-1), the rotating arm 40 is placed in its parking position (step P8-2)

Figure 5E:
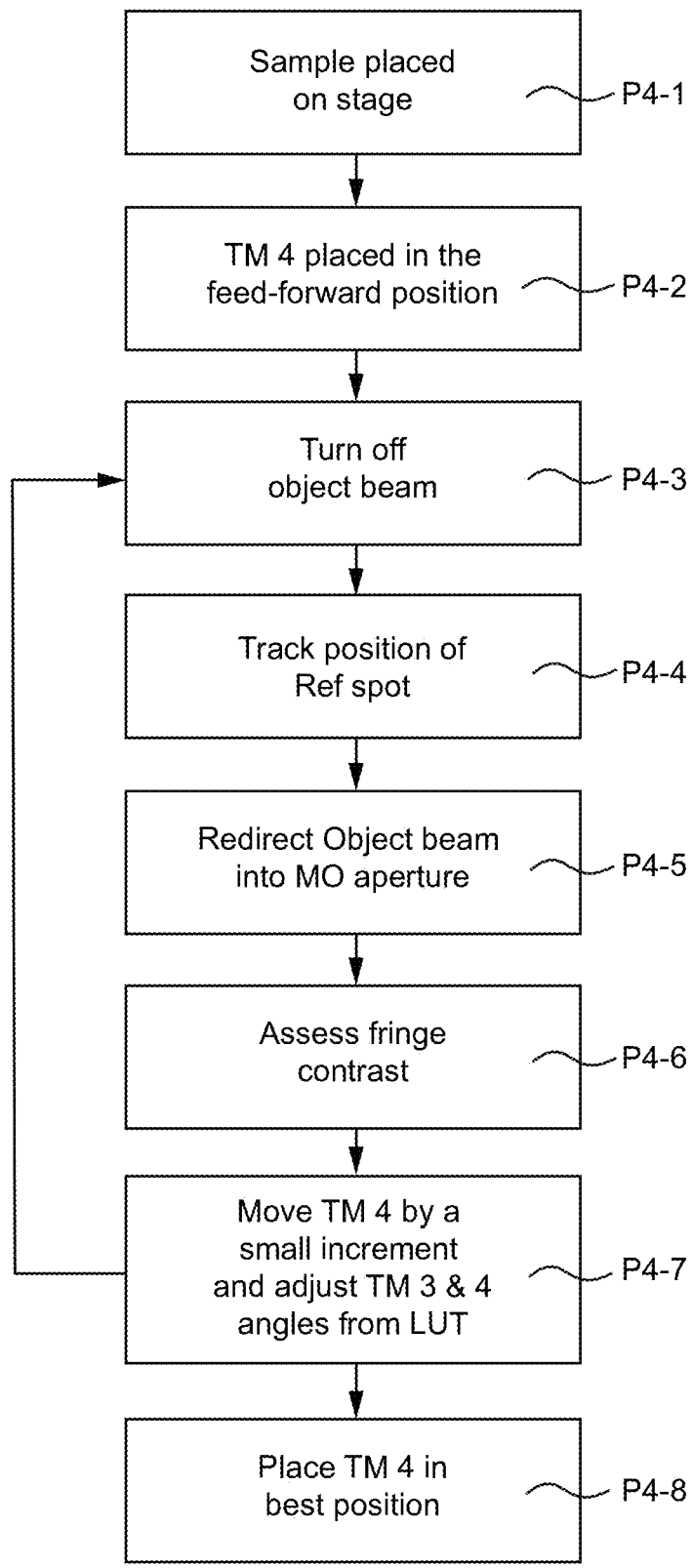

The procedure P4 (illustrated in FIG. 5e) is then launched (step P8-3) to find the optimum OPD position for this arm position leading to the maximum fringe contrast.

The OPD system parameters are saved for this arm position (step P8-4).

The scanning arm is then rotated by a small increment (step P8-5) and the procedure P4 is then launched again. The parameters are again stored.

The previous steps P8-3 to P8-5 are repeated until the arm is back to its parking position.

A look-up table (LUT) is thus created (step P8-6), gathering the parameters that must be applied to the OPD system 32 synchronously with the rotating beam system 36.

LIST OF REFERENCES microscope 2
  (coherent) light source 4 (laser)
  Reference beam 7a
  Sample illumination beam 7b (also named herein object beam)
  light beam guide system 6
    beam splitter 14
    sample beam optical path 20
      direction change mirrors 26, 26a, 26b
        tiltable mirrors TM1 (MEMS)
      sample illumination device 28
        mirror system 34
          first mirror 54
          second mirror 56
        rotating beam system 36
          drive 38
          transmission 39 (belt)
          support 40 (rotating arm—embodiment FIG. 1a, 1b, 1d, 7a,/fixed-embodiments FIG. 7b, 7c)
          actionable mirrors
          hollow axis 58
          bearings 59
          mirror support body 60
          pivoting beam configured to rotate
        microscope objective 37
    reference beam optical path 22
      direction change mirrors 30
        tiltable mirrors TM2, TM3, TM4 (e.g. MEMs mirrors)
        mirror surface 61
        pivot axis 63
      optical path difference (OPD) adjustment device 32
        first light deviating element 42
        second light deviating element 44
        pivot supports 46, 48
          pivot axis 49, 51
          teeth 50
    lens 65 (also named herein field lens)
    beam reuniter 16 light sensing system 8 (detector, camera)
image data processing system 10
housing/support structure 12
    sample observation zone 17
        sample holder 18
            height adjustment mechanism
        sample light
control system 15
    mirror (e.g MEMS mirror) tilt angle control
    Mirror rotation drive control
    Source control
    Camera control
sample 1
    closed containing system 3a
        base 11
        coverslip 9
            observation plane 13
        seal 7
    open dish 3b
        buffering medium 5

The invention claimed is:

1. Microscope comprising:
a light source producing a light beam,
a light beam guide system comprising
    a beam splitter configured to split the light beam into a reference beam and a sample illumination beam passing through the light beam guide system directed by at least one direction change mirror being pivotally actionable (TM1, TM2, TM3, TM4) to guide the reference beam and sample beam along their respective optical paths,
    a sample observation zone configured to receive a sample to be observed in a path of the sample illumination beam,
    a beam reuniter configured to reunite the reference beam and sample illumination beam after passage of the sample illumination beam through the sample observation zone,
a light sensing system configured to retrieve at least phase and intensity values of the light beam downstream of the beam reuniter, and
a control system,
wherein the control system is configured to generate a mirror angle control signal to automatically control an angle of said at least one pivotally actionable direction change mirror, the mirror angle control signal being based at least partially on a signal received, by means of a feedback loop of the control system, from the light sensing system and generated by the light beam.

2. Microscope according to claim 1, wherein said signal received from the light sensing system and generated by the light beam on which the mirror angle control signal is based include any one or more of intensity, coherence, fringe frequency and phase of the light beam received by the light sensing system.

3. Microscope according to claim 1, wherein said at least one pivotally actionable mirror (TM1) is positioned in the sample illumination beam path to correct deviances in the optical path of the sample illumination beam and/or adjustment of the sample illumination angle of the beam.

4. Microscope according to claim 3, wherein the pivotally actionable mirror (TM1) is positioned essentially above the sample observation zone in line with an optical axis of a microscope objective.

5. Microscope according to claim 1, wherein said at least one pivotally actionable mirror is positioned in the reference beam path.

6. Microscope according to claim 5 wherein pivotally actionable mirrors are positioned before, after, or as part of an optical path difference (OPD) system configured to correct deviances of the reference beam in the OPD system.

7. Microscope according to claim 1, wherein at least one pivotally actionable mirror (TM2) is positioned between an optical path difference (OPD) device and the beam reuniter configured for creation and adjustment of interferometric signal captured by the light sensing system.

8. Microscope according to claim 1 further comprising an optical path difference (OPD) adjustment device positioned in an optical path of the reference beam, the OPD adjustment device configured to adjust the optical path length of the reference beam relative to the sample illumination beam, the OPD adjustment device comprising a first pivotally adjustable light deviating element and a second pivotally adjustable light deviating element, each comprising a transparent or reflective material positioned in the optical path of the reference beam, whereby angles of inclination of the light deviating elements are controlled by the control system to adjust the optical path difference.

9. Microscope according to claim 1, wherein said pivotally actionable mirrors are MEMS type components.

10. Microscope according to claim 1, comprising a sample illumination device configured to direct the sample illumination beam through the sample observation zone and into a microscope objective, the sample illumination device comprising a mirror system configured to direct the sample illumination beam at a non zero illumination angle (a) with respect to an optical axis (A) of the microscope objective, and a rotating beam system configured to rotate the angled sample illumination beam around the optical axis.

11. Microscope according to claim 1 further comprising a data processing system configured to receive a plurality of image frames data from the light sensing system, said plurality of image frames being generated for at least a 360° rotation of the sample illumination beam around the microscope objective optical axis.

12. Microscope according to claim 11, wherein the number of frames per 360° captured by the light sensing system and data processing system is greater than 10.

13. Microscope according to claim 12, wherein the image frames data are reconstituted by the data processing system, or supplied by the data processing system to a computing system, for processing into a three dimensional image of the microscopic object.

14. Microscope according to claim 13, wherein the image frames data are further employed by the data processing system, or supplied by the data processing system to a computing system, for estimating optical properties of the sample to improve the three dimensional image of the microscopic object.

15. Microscope according to claim 1, wherein the microscope is configured to generate a three-dimensional image of the microscopic object based on the refractive index of sections of the microscopic object by determining the phase shift of the sample illumination beam after passing through the microscopic object.

16. Microscope according to claim 10, wherein the mirror system of the sample illumination device is mounted in a rotating support and the rotating beam system is formed by the rotating support and a motor drive to rotate the support.

17. Microscope according to claim 10, wherein the rotating beam system comprises rotating tilt actionable mirrors to direct the sample illumination beam on the mirror system of the sample illumination device and wherein the mirror system is mounted on a fixed support.

18. Microscope according to claim 8, wherein at least one of the first pivotally adjustable light deviating element and second pivotally adjustable light deviating element is a pivotally actionable mirror reflecting the reference beam.

\* \* \* \* \*